(12) United States Patent
Baum et al.

(10) Patent No.: US 8,882,889 B2
(45) Date of Patent: Nov. 11, 2014

(54) RECOVERY OF XE AND OTHER HIGH VALUE COMPOUNDS

(75) Inventors: Thomas H. Baum, New Fairfield, CT (US); J. Donald Carruthers, Fairfield, CT (US); Richard Fricke, Paradise Valley, AZ (US); Joshua B. Sweeney, Katonah, NY (US); James V. McManus, Bethel, CT (US); Edward A. Sturm, New Milford, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 27 days.

(21) Appl. No.: 13/704,552

(22) PCT Filed: Jun. 22, 2011

(86) PCT No.: PCT/US2011/041420
§ 371 (c)(1),
(2), (4) Date: Jan. 11, 2013

(87) PCT Pub. No.: WO2011/163342
PCT Pub. Date: Dec. 29, 2011

(65) Prior Publication Data
US 2013/0112076 A1 May 9, 2013

Related U.S. Application Data

(60) Provisional application No. 61/358,843, filed on Jun. 25, 2010.

(51) Int. Cl.
*B01D 53/02* (2006.01)
*B01J 20/28* (2006.01)
(Continued)

(52) U.S. Cl.
CPC ...... *B01D 53/1418* (2013.01); *B01D 2253/308* (2013.01); *B01J 20/28042* (2013.01); *B01D 53/002* (2013.01); *B01J 20/20* (2013.01); *B01D 53/68* (2013.01); *B01D 2257/102* (2013.01); *B01D 2259/402* (2013.01); *G01T 1/178* (2013.01); *B01D 53/02* (2013.01); *B01D 2253/102* (2013.01); *B01J 20/28011* (2013.01); *B01D 53/0476* (2013.01); *B01D 2253/31* (2013.01); *B01D 2258/0216* (2013.01); *C01B 2210/0098* (2013.01); *B01D 2257/2047* (2013.01); *C01B 2210/0037* (2013.01); *C01B 23/0063* (2013.01); *B01D 53/75* (2013.01); *B01D 2256/18* (2013.01); *B01D 2259/4146* (2013.01); *C01B 2210/0046* (2013.01); *B01J 20/2808* (2013.01)
USPC .......................... 95/127; 423/445 R; 96/108

(58) Field of Classification Search
USPC .......................... 95/127; 423/445 R; 96/108
See application file for complete search history.

(56) References Cited

U.S. PATENT DOCUMENTS 3,803,802 A * 4/1974 Schroter et al. ................. 95/127
4,847,494 A 7/1989 Alvarez
(Continued)

FOREIGN PATENT DOCUMENTS

WO 03092778 A1 11/2003

OTHER PUBLICATIONS

Air Products and Chemicals, Inc., "XeCovery: A New Onsite Xenon Recovery Service by Air Products", www.airproducts.com/electronics/technologies/xecovery.htm (Accessed on Jun. 4, 2010), pp. 1-2.

*Primary Examiner* — Christopher P Jones
(74) *Attorney, Agent, or Firm* — Hultquist, PLLC; Steven J. Hultquist; John Pillion

(57) ABSTRACT

A system and method for recovering high value gas from a process stream, material or environment containing same, e.g., xenon by contacting gas from the process stream, material or environment with a carbon adsorbent effective to sorptively capture same, free of or with reduced concentration of fluid species present with the high value gas in the high value gas-containing gas in the process stream, material or environment. Other aspects of the disclosure include a radon detection method and product.

20 Claims, 15 Drawing Sheets

(51) Int. Cl.
  *B01D 53/00* (2006.01)
  *B01J 20/20* (2006.01)
  *B01D 53/68* (2006.01)
  *G01T 1/178* (2006.01)
  *B01D 53/14* (2006.01)
  *C01B 23/00* (2006.01)
  *B01D 53/047* (2006.01)
  *B01D 53/75* (2006.01)

(56) References Cited

U.S. PATENT DOCUMENTS

| | | | |
|---|---|---|---|
| 4,920,270 | A | 4/1990 | Grodzins |
| 6,939,394 | B2 * | 9/2005 | Carruthers ............... 96/108 |
| 7,285,154 | B2 | 10/2007 | Karwacki, Jr. et al. |
| 7,455,719 | B2 | 11/2008 | Carruthers |
| 2003/0000385 | A1 | 1/2003 | Kawai et al. |
| 2009/0107331 | A1 | 4/2009 | Urakami |
| 2012/0210872 | A1 * | 8/2012 | Duan et al. ............... 95/127 |

* cited by examiner

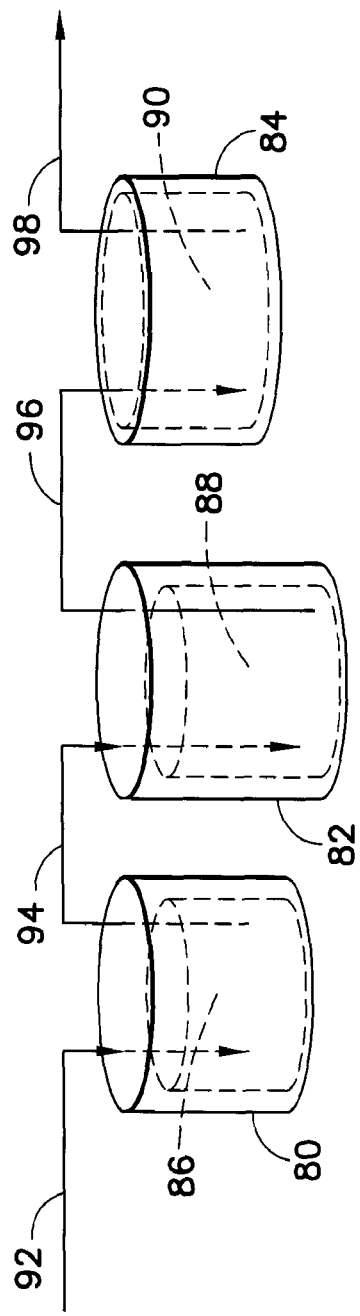
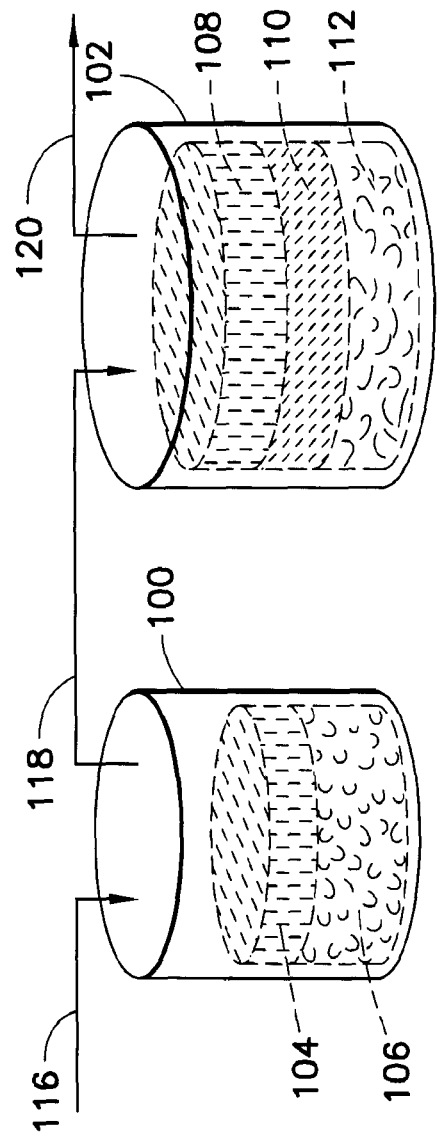

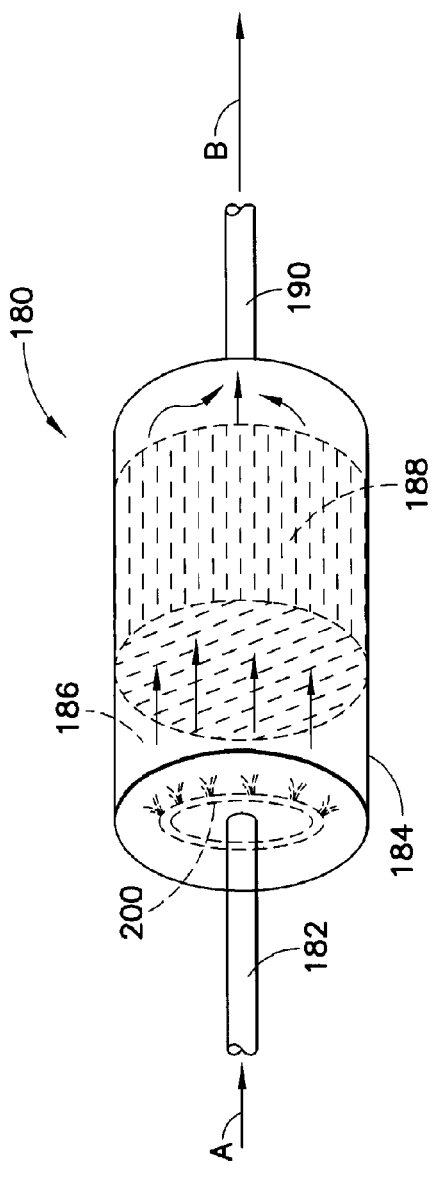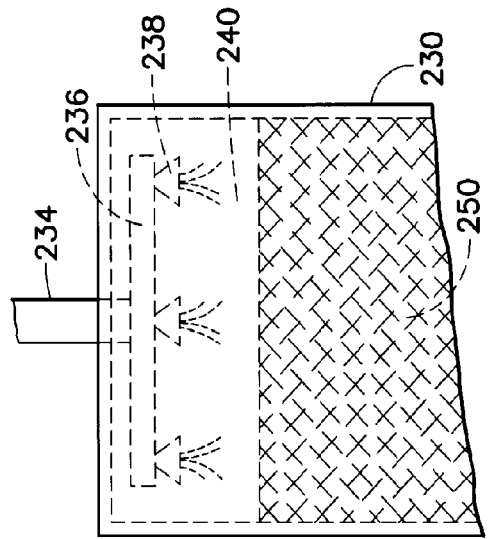
FIG.7
FIG.8
FIG.9

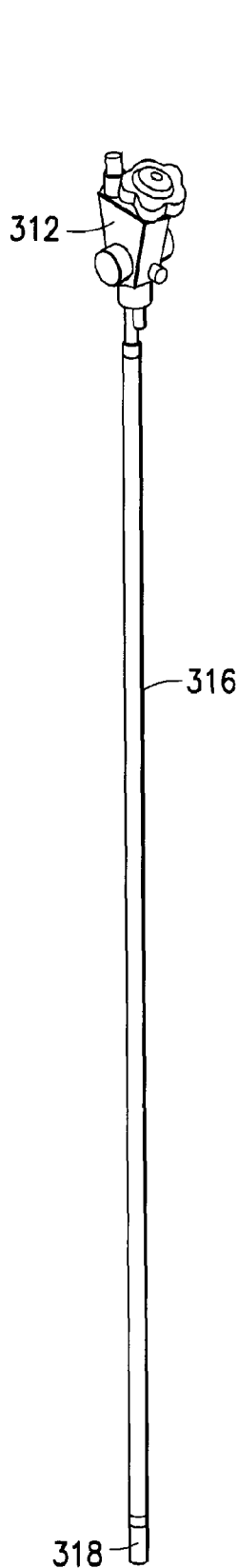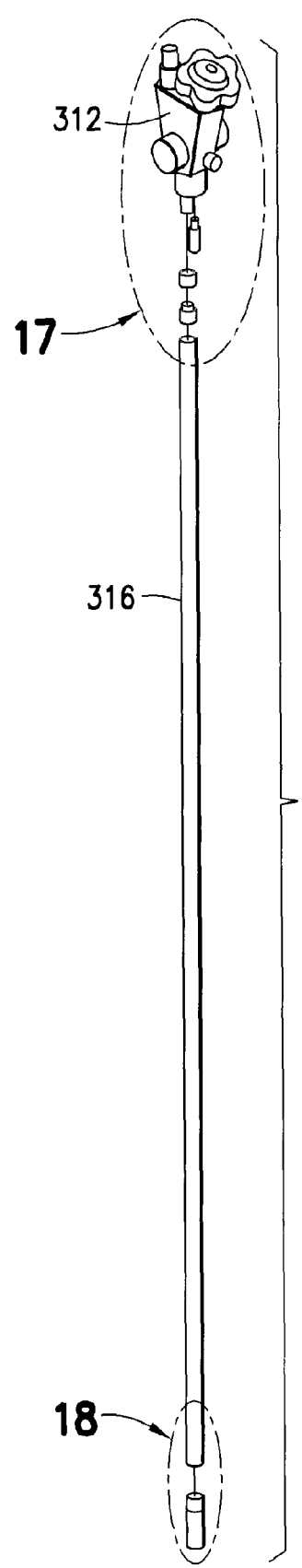
FIG.15
FIG.16

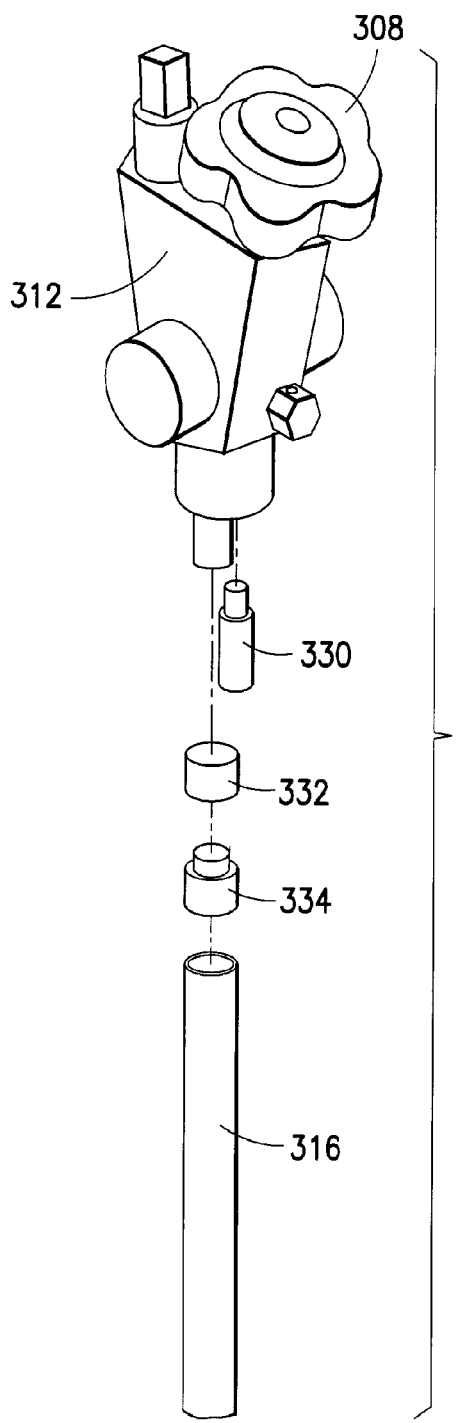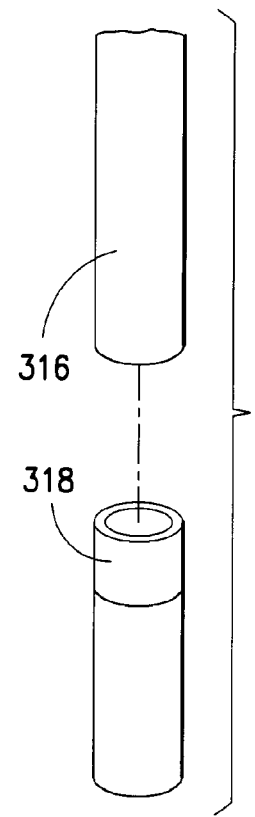
FIG.17
FIG.18

RECOVERY OF XE AND OTHER HIGH VALUE COMPOUNDS

CROSS-REFERENCE TO RELATED APPLICATION(S)

This application is a U.S. national phase application under the provisions of 35 U.S.C. §371 of International Patent Application No. PCT/US11/41420 filed Jun. 22, 2011, which in turn claims the benefit of priority under 35 USC 119 of U.S. Provisional Patent Application No. 61/358,843 filed on Jun. 25, 2010. The disclosures of such international patent application and U.S. provisional patent application are hereby incorporated herein by reference in their respective entireties, for all purposes.

FIELD

The present invention relates to adsorptive recovery of compounds from a process stream, material or environment containing same.

DESCRIPTION OF THE RELATED ART

In many commercial processes and industrial applications, gaseous materials are produced or otherwise present, which are susceptible to loss or degradation if not recovered, recirculated, and/or reprocessed. Such materials may be byproducts of chemical reactions or treatment processes, incompletely consumed gases in gas-utilizing applications, gaseous effluents in mineralic extraction operations, etc.

These gaseous materials may have substantial value as recirculated feedstock or reagents, or as raw materials for further processing or use. These materials may also be a significant source of contamination in the ambient environment of the process or associated facility, and therefore require capture to prevent such contamination from taking place.

SUMMARY

The present disclosure relates to adsorptive recovery of compounds from a process stream, material or environment containing same.

The disclosure in one aspect relates to a method of recovering xenon gas from a process stream, material or environment containing same, comprising contacting xenon-containing gas from such process stream, material or environment with a carbon adsorbent effective to sorptively capture same, free of or with reduced concentration of fluid species initially present with said xenon in said xenon-containing gas in said process stream, material or environment, wherein the carbon adsorbent has a bulk density in a range of from 750 to 1300 kg per cubic meter ($kg/m^3$), and a porosity in which the majority of pores are in a range of from 5 to 8 Angstroms.

The disclosure in another aspect relates to a xenon capture apparatus, comprising:

a containment vessel;

a carbon adsorbent in the containment vessel, wherein the carbon adsorbent is selective for xenon gas, has a bulk density in a range of from 750 to 1300 kg per cubic meter ($kg/m^3$), and a porosity in which the majority of pores are in a range of from 5 to 8 Angstroms.

In a further aspect, the disclosure relates to a radon monitoring assembly, comprising:

a container;

a cap engageable with said container to enclose an interior volume of the container;

a carbon adsorbent in said container, said carbon adsorbent being selective for radon in relation to atmospheric gases; and written indicia comprising instructions for use of the radon monitoring assembly.

Another aspect of the disclosure relates to a method of detecting radon contamination in a locus susceptible to presence or incursion of radon, comprising placing a radon monitoring assembly as described above in an uncapped state in said locus to enable contact of said carbon adsorbent with ambient gas, and recapping the container after a predetermined period of time to provide a contained sample for analytical testing for radon contamination.

The disclosure relates in a still further aspect to a method of recovering high-value gas from a process stream, material or environment containing same, such method comprising contacting the process stream, material or sample from the environment with a carbon adsorbent selective for said high-value gas. Such carbon adsorbent can have a bulk density in a range of from 750 to 1300 kg per cubic meter ($kg/m^3$), and a porosity in which the majority of pores are in a range of from 5 to 8 Angstroms.

In another aspect, the disclosure relates to a system for recovering high-value gas from a process stream, material or environment containing same, such system comprising a carbon adsorbent arranged for contacting said process stream, material or sample from the environment to sorptively capture the high-value gas. The carbon adsorbent can have a bulk density in a range of from 750 to 1300 kg per cubic meter ($kg/m^3$), and a porosity in which the majority of pores are in a range of from 5 to 8 Angstroms.

In a further aspect, the disclosure relates to a carbon adsorbent having a bulk density in a range of from 750 to 1300 kg per cubic meter ($kg/m^3$), and a porosity in which the majority of pores are in a range of from 5 to 8 Angstroms.

Other aspects, features and embodiments of the disclosure will be more fully apparent from the ensuing description and appended claims.

BRIEF DESCRIPTION OF THE DRAWINGS

FIG. 3 is a schematic representation of a series-connected array of adsorbent vessels, which may be utilized for recovery of high-value gas.

FIG. 4 is a schematic representation of series-connected arrangement of adsorbent vessels, in which each adsorbent vessel contains multiple adsorbent beds of different adsorbent media.

FIG. 7 is a schematic representation of an adsorbent vessel, containing an adsorbent bed, in which feed gas is introduced through a distributor member having multiple gas flow orifices about the perimeter thereof.

FIG. 8 is a schematic vertical elevation view, in cross-section, of an adsorbent vessel containing a showerhead device by which influent gas is introduced for contacting with the adsorbent bed in the vessel.

FIG. 9 is a schematic vertical elevation view, in cross-section, of an adsorbent vessel containing a manifold device by which influent gas is introduced for contacting with the adsorbent bed in the vessel

FIG. 15 is a perspective view of the valve head and dip tube assembly of the fluid capture vessel of FIGS. 11-14.

FIG. 16 is an exploded perspective view of the valve head and dip tube assembly of FIG. 15.

FIG. 17 is an exploded perspective view of an upper portion of the valve head and dip tube assembly of FIG. 15.

FIG. 18 is an exploded perspective view of a lower portion of the dip tube assembly of FIG. 15.

DETAILED DESCRIPTION

Figure 1:
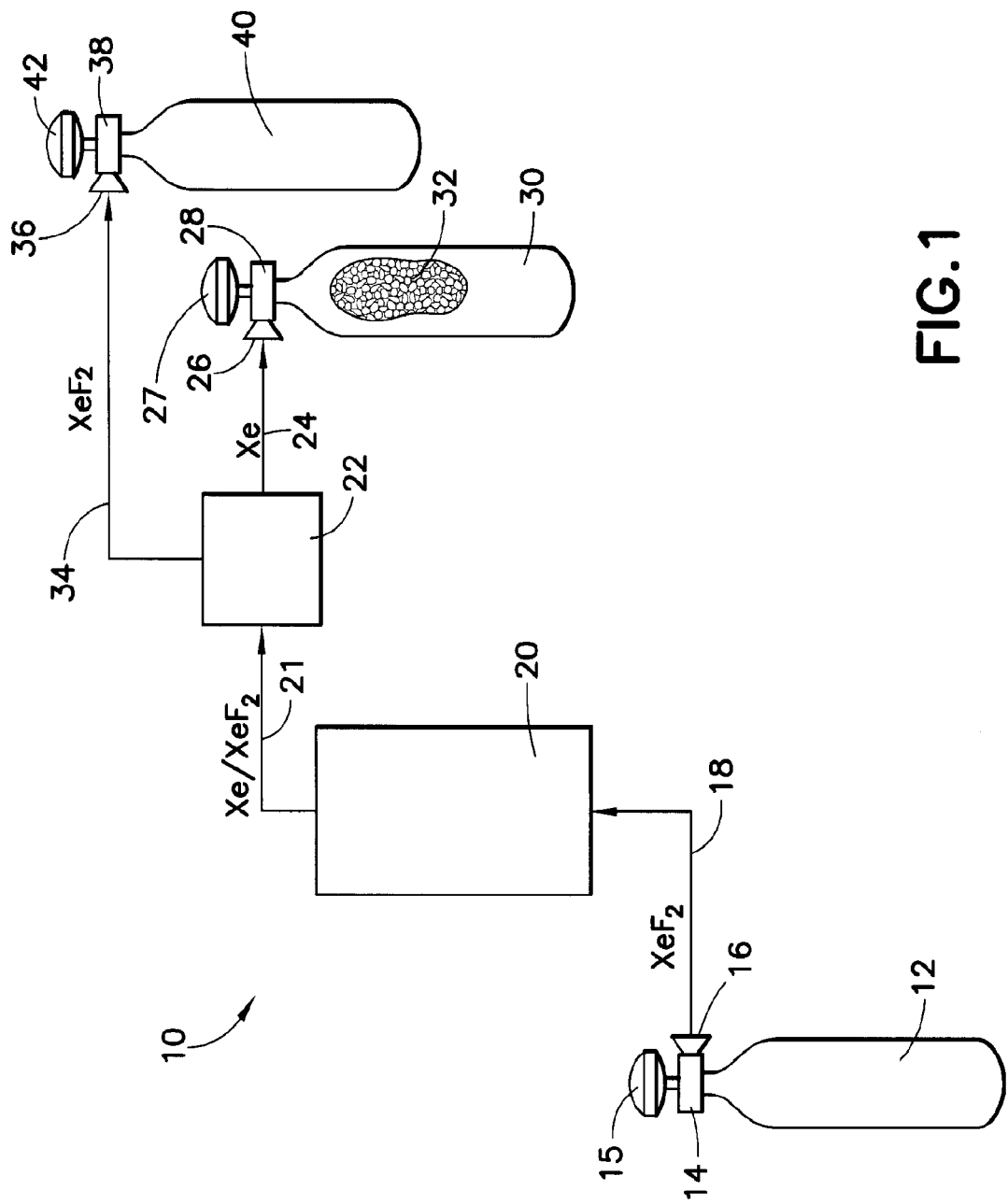
FIG. 1 is a schematic representation of a xenon difluoride cleaning system, in which xenon-containing effluent from the cleaning operation is processed for separation of xenon from xenon difluoride, and capture of the xenon byproduct.

The present disclosure is based on the discovery that extremely efficient adsorptive recovery of high-value gases such as xenon can be achieved utilizing carbon adsorbent having a bulk density in a range of from 750 to 1300 kg per cubic meter ($kg/m^3$), and a porosity in which the majority of pores are in a range of from 5 to 8 Angstroms. Such carbon adsorbent desirably has a volumetric sorptive capacity for xenon, measured at temperature of 273° Kelvin and 1 bar pressure, of at least 125. The carbon adsorbent of such type desirably is characterized by a separation factor $\alpha_{Xe,N}$, in relation to xenon and nitrogen, which is in a range of from 2 to 12.

It has been found that carbon adsorbents of the foregoing characteristics enable effective adsorbent recovery of high-value gases such as xenon to be accomplished in a very compact sorbent arrangement having a small footprint in the facility in which same is used, e.g., a semiconductor manufacturing facility.

In specific embodiments, the carbon adsorbent may have a bulk density in a range of from 800 to 1200 $kg/m^3$, and in still other embodiments, the carbon adsorbent may have a bulk density in a range of from 1000 to 1150 $kg/m^3$.

In specific embodiments, the carbon adsorbent utilized in recovery of high-value gases such as xenon may have a volumetric capacity for xenon adsorption that is, in some embodiments, in the range of from 125 to 150 volumes/volume (v/v), as measured at 273° Kelvin one bar pressure. In other embodiments, the volumetric xenon capacity of the carbon adsorbent may be in a range of from 125 to 145, and in still other embodiments, the volumetric capacity of the carbon adsorbent can be in a range of from 128 to 140, as measured on a volumetric basis at the aforementioned standard temperature and pressure conditions.

Activated carbon adsorbents of such type are particularly advantageous for the separation and recovery of xenon gas in gas mixtures containing nitrogen as the major gas component in the mixture, in which xenon is present at least at part per million levels.

Considering the characterization of carbon adsorbents of the present disclosure that are advantageously employed to recover high-value gases such as xenon from gas mixtures containing same, equilibrium selectivity of the adsorbent material may be utilized as a parameter to describe the ability of the adsorbent to separate xenon from a xenon/nitrogen gas mixture. Equilibrium selectivity of the carbon adsorbent for such xenon/nitrogen gas mixture reflects the differential affinity of the carbon adsorbent for the respective xenon and nitrogen species of such gas mixture. Carbon adsorbents of the present disclosure are highly sorptive for xenon. Their equilibrium selectivity can be expressed by the equation $$\alpha_{Xe,N} = (n_{Xe}/n_N)(p_{Xe}/p_N)$$

in which $\alpha_{Xe,N}$ is the separation factor of the carbon adsorbent for the xenon/nitrogen gas mixture, with n being the amount of the specific component adsorbed, and p being the partial pressure of the specific component in the gas mixture.

As discussed above, carbon adsorbents of the present disclosure desirably have a separation factor $\alpha_{Xe,N}$ for xenon/nitrogen gas mixtures that is in a range of from 2 to 12. In some specific embodiments, the separation factor $\alpha_{Xe,N}$ of the carbon adsorbent is in a range of from 3 to 10. In still other embodiments, the separation factor $\alpha_{Xe,N}$ has a value of at least 5. In yet other embodiments, the separation factor $\alpha_{Xe,N}$ has a value of from 4 to 8.

The carbon adsorbent of the present disclosure is advantageously used to adsorptively recover high-value compounds from a process stream, material or environment containing same, e.g., in arrangements for recovery of high-value gases for reuse, recirculation or other disposition that realize value otherwise lost in the absence of such recovery.

As used herein, the term "high value," in reference to recovered gases, compounds, and fluids, refers to such materials as having significant value upon recovery thereof, as compared to (i) the loss, dissipation or degradation of such materials if not recovered and/or (ii) the cost of remediation, abatement or other necessary action incurred in the absence of recovery of such materials as a result of their loss, dissipation or degradation in the environment.

While the ensuing description is directed primarily to gases as the high-value "recoverable" in various embodiments of this disclosure, it will be recognized that recovery arrangements and processes of the disclosure may be usefully employed and adapted for recovery of fluids generally, including gases, liquids, vapors, supercritical fluids, and the like.

Carbon adsorbents useful for recovery of high-value materials in processes of the present disclosure can be employed to recover a wide variety of recoverable(s) of interest that are susceptible to adsorption of gas in pores of 5-8 Å size. Carbon adsorbents contemplated in this respect includes those containing significant porosity in pores of 5-8 Å size, preferably a major part, e.g., >50% by volume, of the total porosity of such material being in such pore diameter regime. Particularly advantageous carbon adsorbents of such type may have 55%, 60%, 65%, 70%, 75%, 80%, 85%, 90%, 95% or more, by volume, of the total porosity of such material being in pores of 5-8 Å size. Carbon adsorbents of such type can be formed by pyrolysis of polymeric starting material, such as a polyvinylidene chloride polymeric material, in which the pyrolysis and/or post-pyrolysis steps are carried out to impart such porosity.

Carbon adsorbents useful in such respect can be in any suitable form, such as powders, e.g., powders having uniform particle diameter or powder is constituted by particles having a range of particle sizes, e.g., within a range of 20 to 500 µm. Carbon adsorbents can be utilized in the form of beads/extrudates, e.g., having dimensions in a range of from 0.6 to 15 mm, or monolithic articles, e.g., having characteristic dimensions greater than 100 mm Preferred carbon adsorbents preferably are constituted by non-graphitizing, or hard, carbon, having a non-crystalline or microcrystalline (disordered) morphology. Preferably, the adsorbent material is a pyrolyzed activated carbon in the form of a monolith, e.g., as blocks, bricks, pucks, cylinders, rods, or the like. Alternatively, the carbon adsorbent is advantageously provided in a particulate form, e.g., as beads or powder.

The carbon adsorbents of the present disclosure are readily utilized to recover high-value fluid component(s) by contacting the carbon adsorbent with a fluid volume, stream or environment containing such component(s). The carbon adsorbent may be utilized in the form of a bed, e.g., of monolithic or particulate sorbent articles, in a capture or recovery vessel into which or through which the fluid containing the high-value component is passed. Alternatively, the carbon adsorbent may be utilized in an adsorbent bed in a vessel that is adapted for pressure swing adsorption and/or temperature swing adsorption processing, in which fluid containing the high-value fluid component is contacted with the adsorbent bed in the vessel, to sorptively capture the high-value fluid component. The bed thereafter is desorbed, e.g., by pressure blowdown and/or purge gas flow and/or by heating of the bed to desorptively release the adsorbed high-value fluid component.

Activated carbon material adsorption systems are described in the following U.S. patents, the disclosures of which are incorporated by reference herein in their entirety: U.S. Pat. No. 6,743,278 to Carruthers; U.S. Pat. No. 5,518,528 to Tom et al.; U.S. Pat. No. 5,985,008 to Tom et al.; U.S. Pat. No. 5,761,910 to Tom; U.S. Pat. No. 5,916,245 to Tom; U.S. Pat. No. 6,764,755 to Tom et al.; U.S. Pat. No. 6,991,671 to Brestovansky et al.; U.S. Pat. No. 6,027,547 to Tom et al.; U.S. Pat. No. 6,019,823 to Tischler et al.; U.S. Pat. No. 5,917,140 to Tom; U.S. Pat. No. 5,993,766 to Tom et al.; U.S. Pat. No. 5,704,965 to Tom et al.; U.S. Pat. No. 5,707,424 to Tom et al.; and U.S. Pat. No. 5,704,967 to Tom et al.

For specific applications, the pore size distribution of carbon adsorbents of the present disclosure may be "tuned" by as little as tenths of Angstroms, such as for example by varying the polymeric starting material, pyrolysis conditions and post-pyrolysis processing to achieve a carbon adsorbent material that is suitable for a given recovery of high value fluid. In this respect, the characterization of the adsorbent can be carried out using porosimeters, probe molecule porosimetry, Raman spectroscopy, x-ray diffraction, scanning electron microscopy and optical microscopy, and other equipment known within the skill of the art for characterization of adsorbent materials, to determine the starting materials, process conditions and resulting characteristics for use in preparing carbon adsorbents of the present disclosure.

Concerning thermophysical properties of activated carbons that may be usefully employed in specific recovery applications in accordance with the present disclosure, Table 1 below sets out values for illustrative ranges of various thermophysical characteristics that may be applicable to activated carbon adsorbents having a monolithic form, as useful for recovery of high-value fluid species, as well as particular thermophysical characteristics of an illustrative pyrolyzed, monolithic activated carbon adsorbent of the present disclosure.

TABLE 1

| Thermophysical property | Illustrative thermophysical property range for various representative activated carbon monolith adsorbents | Illustrative thermophysical property value of a specific monolith for recovery of fluid species |
|---|---|---|
| bulk density, kg m$^{-3}$ | 750-1300 | 1120 |
| thermal conductivity, Wm$^{-1}$K$^{-1}$ | 0.44-1.20 | 0.92 |
| limiting concentration (NH$_3$), kg · kg$^{-1}$ carbon | 0.15-0.36 | 0.24 |
| radial permeability, K$_r$m$^2$ | 1000 – 3500 × 10$^{-16}$ | 9 × 10$^{-16}$ |
| specific heat, J kg$^{-1}$ K$^{-1}$ | 800-1080 | 1000 |
| Xenon capacity (V/V), 273K, 1 bar | 125-145 | 135 |

It will be recognized that the character of the carbon adsorbent can be widely varied within the practice of the present disclosure, to provide an adsorbent material for a particular fluid recovery application. As further specific examples, Table 2 below sets forth characteristics of two illustrative carbon adsorbents, designated "Carbon Adsorbent A" and "Carbon Adsorbent B," respectively, having utility for recovery of xenon.

TABLE 2

| Property | Carbon Adsorbent A | Carbon Adsorbent B |
|---|---|---|
| bulk density, kg m$^{-3}$ | 1120 | 1120 |
| Xenon capacity (V/V), 273K, 1 bar | 136 | 130 |
| Xenon micropore volume (mL/g), 273K, 1 bar | 0.370 | 0.355 |
| Neopentane micropore volume (mL/g), 273K, 1 bar | 0.295 | 0.007 |

Carbon Adsorbent A has utility for capturing xenon when present in a dilute concentration in mixture with nitrogen. Carbon Adsorbent B has utility for preferentially recovering xenon in a nitrogen gas stream that also contains molecules larger in size than xenon, by size-exclusion molecular sieving. Table 2 shows the bulk density of each of the carbon adsorbents, the adsorption capability of such adsorbents for xenon, on a volumetric basis, at standard conditions (273° Kelvin, one bar pressure), xenon micropore volume as determined at such standard conditions, and neopentane micropore volume, as likewise determined at such standard conditions.

One advantage of utilizing carbon adsorbent monoliths as the carbon adsorbent in applications of the present disclosure is that such structural form of the carbon adsorbent provides high sorbate capacity per unit volume, high thermal conductivity, and the ability to be manufactured to satisfy close-tolerance geometric specifications as a single piece (as opposed to granular or beaded adsorbent forms which tend to attrit over time).

In various embodiments, carbon adsorbents having a high fill capacity are employed, e.g., in the form of porous carbon adsorbent discs in a stacked array. Such a stacked array of carbon adsorbent may be disposed in a fluid capture and storage vessel for recovery of fluid species for which the carbon adsorbent has appropriate sorptive affinity. The fill capacity of the porous carbon adsorbent is the amount of adsorbate that can be taken up by the adsorbent, i.e., the loading of the adsorbate species on the adsorbent at standard or other specified conditions.

For particular applications, the loading capacity of the porous carbon adsorbent can be significantly increased, by processing the adsorbent via a procedure in which the adsorbent is first contacted with a swelling agent, followed by contacting of the carbon adsorbent with a pressurized gaseous penetration agent, followed by removal of the swelling agent and penetration agent, e.g., by vacuum extraction and heating of the porous carbon to volatilize any residual swelling agent and penetration agent therein.

As used in such context, the term "swelling agent" refers to an agent that in contact with the microstructure of the porous carbon material, effects an expansion of the porosity and void structure of such material. The swelling agent may be of any suitable type, and may for example include agents such as water, ethers, alcohols or other organic or inorganic solvent media that cause such expansion of the porous carbon to take place.

The term "penetration agent" as used herein refers to an agent that (1) in a pressurized form is contacted with the porous carbon material containing the swelling agent to effect transport of the swelling agent into the porosity and void structure for enhancement of the loading capacity of the porous carbon adsorbent material upon its being subsequently contacted by an adsorbate, and (2) is compatible with the swelling agent to permit the swelling agent and penetration agent to be volatilized and removed from the porosity and void structure, without loss of the swelling effect of the swelling agent on such porosity and void structure. The penetration agent may be of any suitable type, and may for example include inert gases such as helium, argon, krypton, neon, etc.

In the one preferred embodiment, the swelling agent comprises water vapor, and the penetration agent comprises helium.

In specific embodiments of the removal of the residual swelling agent and penetration agent from the porosity and void structure of the porous carbon, after swelling has been taking place, it is important that the removal not involve heating to temperatures of 350° C. or higher, since temperatures of 350° C. or higher can result in loss of the increased loading capability that is otherwise obtained when the removal of the swelling agent and penetration agent is effected at temperatures below 350° C.

As a specific example, the carbon adsorbent can be pretreated by exposure to water vapor, so that the carbon adsorbent takes up the water vapor. This water vapor exposure is followed by contact of the carbon adsorbent with helium (or other inert gas, e.g. argon, krypton, nitrogen, xenon) at elevated pressure, such as pressure in a range of from 100 to 500 psi. The helium then is removed from the carbon adsorbent under vacuum, followed by a bake-out at elevated temperature, e.g., temperature in a range of from 100° C. to 300° C. This yields a pretreated carbon adsorbent having enhanced adsorptive capacity for small molecule fluid species.

Such pretreatment method can be advantageously employed for any of a variety of fluid species, and is most beneficially applied for enhancing activated carbon, e.g., in the form of beads, granules, tablets, pellets, powders, extrudates, particulates, cloth or web form articles, monolithic forms, composites of the porous carbon with other materials, comminuted forms of the foregoing, and crushed forms of the foregoing, for use in capture and storage of a gas whose molecules are adsorbed by the carbon adsorbent.

It will be appreciated that the carbon adsorbent can be treated or pretreated in any suitable manner, to increase its sorptive capacity, modify its pore size or pore size distribution, or otherwise prepare the adsorbent for use in recovery of recoverable fluid species.

The present disclosure in one aspect contemplates the use of carbon adsorbent, e.g., a carbon adsorbent of the type described hereinabove, for fast radon and gas screening applications, in which the recoverable gas is radon that is present in an environmental locus, e.g., a residential or commercial building, potential building site, or other environment that may be susceptible to the presence or incursion of radon gas.

The use of nanoporous carbon for rapid detection of radon gas can be effected by a simple vessel containing a particular quantity of carbon adsorbent that is selective for radon gas, wherein the vessel is closed until the protection usage is desired, whereupon the vessel is uncapped, punctured, or otherwise opened, e.g., by removal of a sealing element or other closure member, to effect exposure of the carbon adsorbent in the vessel to the environment in which the vessel is disposed subsequent to such opening. The vessel may be provided with written instructions on or associated with the vessel, concerning the activation and utilization of the nanoporous carbon-containing vessel for radon detection.

Such packaged carbon adsorbent provides a rapid solution for testing of gases in residential and commercial properties, such as is routinely carried out in transactions involving the sale or transfer of rights in real estate. In some cases, routine gas analysis is required within specified geographical regions, due to the geological history of such regions. For example, radon is routinely tested in the Northeast United States as a result of radon formation from geological compositions specific to that region.

Radon monitoring is also increasing worldwide in regions of geological activity, including fault regions (earthquakes) and mountainous volcanic regions. Recent studies have shown an increase in radon production prior to fault movements and resulting earthquakes. See For example http://www.medicaljournal-ias.org/3_3/Khan1.pdf and http://www.accesstoenergy.com/view/atearchive/s76a2283.htm. The present disclosure in specific embodiments contemplates monitoring of radon presence or incursion in order to predict fault movement and/or earthquakes, using high-performance carbon adsorbent materials of the present disclosure for sorptive uptake of such radon gas. Vessels containing carbon adsorbent can readily be utilized for ongoing collection of radon gas from an ambient environment, by exposing a fresh canister at regular intervals and for a predetermined period of time.

For example, a fresh canister may be opened and exposed to an ambient environment at 9 AM each day, for a duration of exposure of one hour, following which the canister is recapped or otherwise closed, with the adsorbent thereafter being heated in a closed test chamber to release adsorbed gas for analysis, e.g., by mass spectrometry, NMR, FTIR, GC-MS, ICP-MS or other analytical technique appropriate for quantitating the amount of radon gas adsorbed by the canister. A longitudinal study of successive gas samples as captured by the corresponding series of canisters exposed to the ambient environment therefore can provide data showing whether radon gas levels are static, decreasing or increasing in character, over a period of time sufficient to support predictive assessment for the environmental locus subjected to monitoring.

Other adsorbent exposure techniques and analytical methods may be employed, to determine safety of a given environment and areas in proximity thereto, with respect to radon gas or other gas species or fluid components of interest.

The present disclosure also contemplates the treatment or modification of carbon adsorbent to enhance its sorptive character for radon, e.g., by tailoring the porosity to optimize radon sorptive capacity of the adsorbent. Such modification can be effected within the skill of the art, based on the disclosure herein, by differential modification of the adsorbent, and empirical testing of the resulting sorbate loading capacity of the appertaining adsorbent.

In this manner, the carbon adsorbent when exposed to the ambient environment quickly adsorbs gases from the environment, enabling analytical monitoring of environmental gases.

In another specific application, the disclosure contemplates use of carbon adsorbent of the present disclosure to recover xenon gas from gas mixtures containing same. Xenon exhibits unique noble gas behavior, such as the formation of xenon difluoride, but xenon is extremely expensive, as a result of its small natural abundance on Earth.

Xenon difluoride has found utility as a cleaning gas in semiconductor manufacturing operations. In one such application, commercially available under the trademark Autoclean® from ATMI, Inc., Danbury, Conn., USA, xenon difluoride in packaged form is provided for cleaning of ion implantation systems, including ion source chambers, and surfaces and components therein. The xenon difluoride in such applications may react with deposits in the ion implantation system, so that the fluorine component of the $XeF_2$ reagent forms a corresponding gaseous fluoride compound with elements of the deposit, to enable the deposit to be removed by such reaction. In specific applications, the xenon difluoride may be subjected to ionization, to create a corresponding plasma for reaction with deposits in the chamber to be cleaned.

In such xenon difluoride cleaning operations, elemental and/or ionic xenon is generated, and becomes a component of the effluent from the cleaning operation. The effluent may be subjected to abatement processes that are ineffective for removing the xenon component. As a result, such xenon component is thereafter vented to the atmosphere, and the significant value of such xenon is thereby lost.

This is also true of other applications of xenon difluoride in semiconductor manufacturing, e.g., for the selective removal of silicon in microelectromechanical systems (MEMS) applications, and in cleaning of chemical vapor deposition (CVD) chambers.

In such applications, xenon difluoride readily disassociates on surfaces, producing atomic fluorine that is highly reactive as an etchant and intermediate. When in contact with arsenic, phosphorus, boron, silicon or germanium, the atomic fluorine readily produces $ASF_3$, $PF_3$, $BF_3$, $SiF_4$ and $GeF_4$ as etch by-products that are readily removed from the implant or CVD chamber.

The present disclosure in specific implementations utilizes the carbon adsorbent to sorptively capture xenon gas for recovery and reuse thereof.

A significant challenge with this approach is that the xenon sought to be recovered is in mixture with xenon difluoride, and xenon difluoride is active to produce fluorination of the carbon adsorbent, leading in turn to its partial degradation. If this degradation continues, it can severely compromise the sorptive capacity and utility of the carbon adsorbent. It has been discovered, however, that the xenon- and xenon difluoride-containing mixture can be submitted to low temperature exposure, to condense xenon difluoride as a solid material, and thereby effect its removal from the $Xe/XeF_2$-containing mixture, prior to contacting the resulting xenon difluoride-reduced fluid with the carbon adsorbent. It has surprisingly been found that xenon difluoride can be rapidly and effectively condensed upstream of the carbon adsorbent, to remove substantially all xenon difluoride from the mixed gas, without carryover or adverse effect of xenon difluoride on the carbon adsorbent.

A particularly effective apparatus configuration in this respect includes a low temperature zone for condensation of xenon difluoride as a solid material, upstream of the carbon adsorbent. The low temperature condensation zone may be located in close proximity to the carbon adsorbent, to take advantage of the increased absorption capacity for the xenon gas incident to lower temperature of gas being contacted with the carbon adsorbent, since adsorbent loading is inversely related to temperature of the adsorbent contacting. There is thus a high degree of synergy achieved by the contemporaneous removal of xenon difluoride and sorptive capture of xenon gas, as the xenon/xenon difluoride gas mixture flows in succession to the low temperature condensation zone and then to the carbon adsorbent.

The low temperature condensation zone and/or the carbon adsorbent zone of the processing system may utilize superatmospheric pressure that is effective both for the solid condensation of xenon difluoride, as a reverse sublimation operation, and for the sorptive capture of xenon gas in the carbon adsorbent zone.

The carbon adsorbent zone may be configured in a suitable manner. In one embodiment, the carbon adsorbent is contained in a xenon capture vessel, as a bed or aggregate mass of the adsorbent, in which the xenon gas stream resulting from the removal of xenon difluoride is flowed into the xenon capture vessel for sorptive removal of the xenon gas by the carbon adsorbent. For this purpose, the vessel may be chilled to reduce the temperature of the adsorbent therein, and thereby correspondingly increase the loading capacity of the adsorbent to ensure rapid and complete capture of the xenon gas.

Following the fill of the xenon capture vessel with xenon gas, the vessel can be closed, e.g., by manual or automatic closure of the valve in the valve head of such vessel, with the vessel thereafter being removed from the chilling apparatus, to subsequently reach equilibrium at an ambient temperature. The xenon capture vessel containing recovered xenon gas then may be transported to a reuse or reprocessing site. In some instances, the purity of the xenon gas may allow its direct reuse from the capture vessel, i.e., with the capture vessel thereafter serving as a storage and dispensing vessel for the xenon gas.

It will be recognized that the xenon- and xenon difluoride-containing gas mixture in the first instance may contain other fluid species, and the gas mixture in conjunction with the low temperature removal of the xenon difluoride and the sorptive capture of the xenon gas, may be subjected to other processing operations, to remove other fluid species from the gas mixture. Such additional processing may be carried out upstream or in advance of the low temperature condensation of xenon difluoride, or subsequent to such condensation removal of xenon difluoride, before the xenon-containing gas produced by such condensation removal of xenon difluoride is submitted to sorptive capture of the xenon gas.

Xenon gas uptake on the carbon adsorbent will occur rapidly. Selectivity for xenon, relative to other gaseous species, can be imparted to the carbon adsorbent during pyrolytic decomposition of a polymeric starting material, or by post-pyrolysis treatment, to provide appropriate pore size and pore size distribution that is specifically tailored for xenon gas adsorption.

The present disclosure contemplates recovery of xenon from xenon/nitrogen gas mixtures, in which such gas mixtures are subjected to processing to remove the nitrogen gas from the mixture, to yield the xenon gas for recirculation, reuse or other disposition. In a specific embodiment, the xenon is recovered from a gas mixture including xenon, nitrogen, silicon tetrafluoride and carbon tetrafluoride.

Other applications of the sorptive capture technology of the present disclosure include recovery of gas species such as krypton, sulfur hexafluoride, carbon tetrafluoride and chlorosilane, from gas mixtures or environments containing same.

Referring specifically to xenon as a representative gas species for such sorptive recovery applications, xenon in addition to the cleaning operations previously described, is usefully employed in a wide variety of processes. In semiconductor manufacturing, in addition to cleaning of ion implant and chemical vapor deposition apparatus, xenon can be used for integrated circuit fabrication involving high aspect ratio etching, as an excitation medium for EUV lithography, and to enable polymer cross-linking for enhanced protection of photoresist during etching operations. Outside of semiconductor manufacturing, xenon is utilized as fuel for ion propulsion engines, in high brightness, low-energy lamps for lighting and displays, as well as in anesthetic and trauma medical applications.

Due to its high value, recovery of xenon is of corresponding importance in applications in which xenon is used. The sorptive capture arrangements of the present disclosure may be integrated with existing processes that isolate xenon for recovery in the first instance. One such existing process is commercially available from Air Products & Chemicals, Inc. (Allentown, Pa., USA) under the trademark XeCovery, in which vacuum swing adsorption (VSA) is utilized, in an arrangement of a type disclosed in U.S. Pat. No. 7,285,154, the disclosure of which is hereby incorporated herein in its entirety. Such XeCovery process is capable of extracting xenon down to part-per-million levels from process streams containing same, to produce an enriched mixture of recovered xenon, typically at low percent levels, which is compressed and stored for subsequent processing by distillation or other recovery technique. This process can be modified in accordance with one aspect of the present disclosure, to effect sorptive capture of xenon from the enriched mixture, e.g., containing nitrogen and xenon, containing percent level concentrations of xenon, with the carbon adsorbent of the present disclosure.

For the recovery of specific recoverable gases, carbon adsorbents can be prepared with specific desired properties for the gas species of interest, e.g., xenon, krypton, radon, carbon tetrafluoride, dicarbon hexafluoride, sulfur hexafluoride, etc. As indicated earlier herein, polyvinylidene chloride (PVDC)-based carbons are highly advantageous and readily amenable to tailoring to specific selectivity, pore size, pore size distribution, pore densities, and loading capacity characteristics, for such applications.

Such tailoring may be effected by pyrolytically decomposing the PVDC starting material, involving de-hydrohalogenation reaction in a controlled manner, to provide the carbon adsorbent in a desired form, e.g., carbon powder, carbon pellets, carbon monoliths, or other suitable form. The decomposition and reaction rates can be selectively varied for controlled formation of the carbon adsorbent with the desired properties.

In the various applications of the present disclosure in which adsorbents are used for capture and recovery of fluid species, the adsorbents may be utilized in varied arrangements. For example, adsorbents may be provided in different vessels, with the vessels being coupled in series arrangement for gas passage through each of the vessels in sequence. Alternatively, parallel arrangements of adsorbent-containing vessels may be employed, in which the adsorbent is utilized as a fixed bed or mass, or alternatively as a fluid as bed, or in other arrangements. In such parallel arrangement, the respective vessels in the array can be arranged by suitable valving, manifolding, etc., to effect switch-over of vessels, so that an off-stream vessel can be regenerated by release of the captured fluid from the adsorbent therein, with passage of the released fluid to a bulk reservoir, reprocessing facility, or other disposition.

Considering a series arrangement of adsorbent-containing vessels, such arrangement permits loading and concentration of the recoverable sorbate species in an initial vessel of the series, before it is fully loaded with the sorbate species, following which such initial vessel can be taken out of service, with the flow of influent gas being directed to a second adsorbent-containing vessel in the array, e.g., while the first vessel is being changed out with a replacement fresh adsorbent-containing vessel being installed in its place. The flow path through the respective vessels can then be modified, so that the fresh vessel becomes the last vessel in the processing arrangement of series-connected vessels, with each vessel during its service life being shifted through the sequence so that it progresses from an initial position in the array of vessels to a second, third, etc. position, in move up, move down or other fashion.

Such a series arrangement is beneficial to ensure complete capture of recoverable sorbable material, so that a subsequent vessel in a series arrangement captures sorbables material that may have escaped sorptive capture in a prior vessel in the series.

Further, such a series arrangement can be arranged for reconfiguration of the flow circuit, for selective isolation or bypass of a specific vessel for replacement or service, or for performing a recovery operation, such as may involve depressurization and/or heating of the vessel, to effect desorption of the recovered sorbables, so that they are passed from the capture vessel to a reservoir, retention facility, reprocessing unit, or other use.

Adsorbent-containing vessels can also be arranged in various embodiments of the present disclosure, on translatable platforms or support structures, with suitable control and monitoring systems, so that the adsorbent-containing vessels in the mounted or supported array are translated, e.g., on a carousel support, into fluid capture relationship with associated flow circuitry, so that the vessel is coupled with a feed line supplying sorbable material, for capture by the adsorbent in the vessel coupled with such feed line. After the requisite fill of the adsorbent-containing vessel coupled with the flow circuitry has been achieved, the vessel array is translated so that the filled vessel is uncoupled, and a new vessel coupled for continuity of operation.

In addition, the present disclosure contemplates arrangements in which the fluid capture vessel contains a multiplicity, e.g., two or more, of different sorbent materials. Thus, the disclosure contemplates fluid capture vessels in which composite adsorbent beds are provided, as mixtures of different adsorbents. Such mixtures may be mixtures of respective particles, granules, pellets or other discontinuous forms of the different adsorbents. The mixtures may also be consolidated into a unitary form, such as composite monoliths, containing different sorbent species having selectivity for different gas components in the gas mixture to be contacted therewith. The monolith may be homogeneous in character, with the dispersion of respective adsorbent components being substantially uniform throughout the monolithic mass. Alternatively, the composite monoliths may be formed with a heterogeneous composition, in which a first adsorbent is localized in a first region of the monolith, a second adsorbent is localized in another region of the monolith, etc. For such a heterogeneous composition, e.g., when using different carbon materials, a monolith can be formed using a layup technique in which sheets or layers of different precursor materials, e.g., polymeric resins, are arranged in a stack which is subsequently pyrolyzed to form the multilayer multi-adsorbent monolith.

Series arrangement of adsorbent-containing vessels are also contemplated in the broad practice of the present disclosure, in which constituent vessels each contain multiple adsorbent species, e.g., as discrete beds in series within a specific vessel, or in other arrangement. In this regard, it may be advantageous in various applications to utilize vessels with interior flow-directing structure, such as plates, baffles, fans, helical dispersing elements, etc.

Such flow-directing structures can be arranged vertically, horizontally, or at any attitude or orientation that is appropriate to provide a desired hydrodynamic flow of gas for contacting of the adsorbent in the vessel. In this manner, the adsorbent-containing vessel may be compartmentalized, for example, to maximize the contact of the fluid stream with the adsorbent or to otherwise to increase the residence time of the fluid stream in the adsorbent-containing vessel, and achieve the requisite capture of the recoverable sorbate species.

In the event that monolithic or block-form adsorbents are employed, the sides and surfaces of the adsorbent articles can be fabricated, treated or configured to modulate, e.g., permit or prevent, flow of the gas containing absorbable species therein, so as to create a desired fluid flow path through the interior volume of the vessel. For example, the monolithic adsorbent may be formed with flow-directing passages therein, so that the overall volume of the adsorbent is most effectively utilized.

Flow of sorbate-containing gas into the fluid capture vessel for contacting with the adsorbent therein may also be facilitated or enhanced by specific fluid introduction arrangements. For example, showerhead or nozzle arrangements may be employed to influent gas over the full cross-sectional extent of the adsorbent bed or monolith.

The fluid capture vessels and processes and systems of the invention may be implemented with various devices, systems and techniques for determining endpoint operation of the fluid capture vessels, i.e., wherein the fluid capture vessel has been loaded to a maximum or otherwise desired loading level, so that the fluid capture vessel can be removed from active capture service. Such endpoint determinations can be made utilizing any suitable arrangements of monitoring, detection and analysis of the level of loading of captured fluid on the adsorbent in the vessel, or array of vessels. For example, endpoint can be determined using a change in the flow rate of gas passed through a fluid capture vessel, or a change in pressure of such gas, or attainment of a specific weight of a fluid vessel indicating loading with a desired or maximum quantity of absorbable fluid, or by totalization of gas contacted with the adsorbent in conjunction with monitoring of concentration of the fluid species of interest, or in any other suitable manner effective to evidence the occurrence or onset of saturation of the adsorbent (or attainment of a specific loading level of the adsorbent) with the recoverable fluid of interest.

It will be recognized that the geometry, confirmation and construction of sorbent-containing vessels for use in accordance with the present disclosure may be widely varied in practice, to achieve specific fluid contacting arrangements and results, in respect of capture of the desired fluid component(s) of the influent gas introduced to the fluid capture vessel.

The features and advantages of the present disclosure, and systems and processes herein disclosed, are more fully appreciated from the ensuing disclosure, with reference to the drawings of FIGS. 1-26 hereof.

Referring now to the drawings, FIG. 1 is a schematic representation of a xenon difluoride cleaning system 10, in which xenon-containing effluent from the cleaning operation is processed for separation of xenon from xenon difluoride, and capture of the xenon byproduct.

In this xenon difluoride cleaning system, a storage and dispensing vessel 12 containing xenon difluoride is coupled at a discharge port 16 with a feed line 18, for dispensing of xenon difluoride. The discharge port 16 is provided by the valve head 14 of the vessel, with the valve head being coupled to a manual adjustment wheel 15 for opening/closing or modulation of the valve in the valve head 14 as desired. In lieu of a manual adjustment wheel 15, the vessel 12 may be arranged with an automatic valve actuator, for automated operation.

The xenon difluoride discharged from the vessel 12 into feed line 18 flows into the process chamber 20 for cleaning of such chamber. The chamber may for example comprise an ion implanter arc chamber, an ion source housing, or other compartment of an ion implanter. The chamber alternatively may comprise a deposition chamber of a chemical vapor deposition (CVD) apparatus. Still further, the chamber may be of any suitable type in which deposits or contaminants are susceptible to removal by flow of xenon difluoride into the chamber in contact with the internal surfaces and components therein.

The cleaning operation conducted in chamber 20 produces an effluent, discharged an effluent discharge line 21, containing xenon in addition to unreacted xenon difluoride deriving from the xenon difluoride stream introduced to chamber 20 in feed line 18.

From the effluent discharge line 21, the xenon- and xenon difluoride-containing gas mixture enters the low temperature separation chamber 22, in which the xenon difluoride in the gas mixture is condensed to solid form, thus disengaging the xenon difluoride from the xenon gas in the influent gas mixture. The separated xenon gas then flows from the low temperature separation chamber 22 in line 24 to the inlet port 26 of the valve head 28 of the xenon fluid capture vessel 30. The valve head 28 includes a manual hand wheel 27, as shown. Alternatively, the xenon capture vessel 30 may be equipped with an automatic valve actuator, for operation of the valve in the valve head 28 of the vessel.

After the xenon gas has been recovered in the fluid capture vessel 40, the refrigeration in the low temperature separation chamber 22 is discontinued, e.g., by shutoff of refrigerant valves, deactuation of the refrigeration unit, or other suitable manner, so that the chamber 22 warms, to effect sublimation of the xenon difluoride to vapor form. The xenon difluoride vapor flows in line 34 to the inlet port 36 of the valve head 38 of xenon difluoride vessel 40, with the valve and valve head 38 being open to accommodate in-flow of the xenon difluoride gas to the vessel 40. The hand wheel 42 of vessel 40 may be manually opened for such purpose, or the manual hand wheel 42 may in turn be absent, in favor of an automated valve actuator assembly, for opening and closing the valve in the valve head 38, as necessary.

By the arrangement shown in FIG. 1, the xenon component of the xenon/xenon difluoride gas mixture is recovered for reuse or other recovery disposition. In the specific arrangement shown, the xenon difluoride is separately recovered, but may alternatively be recycled from line 34 to the feed line 18 or directly to the chamber 20, for reuse in the cleaning operation.

Figure 2:
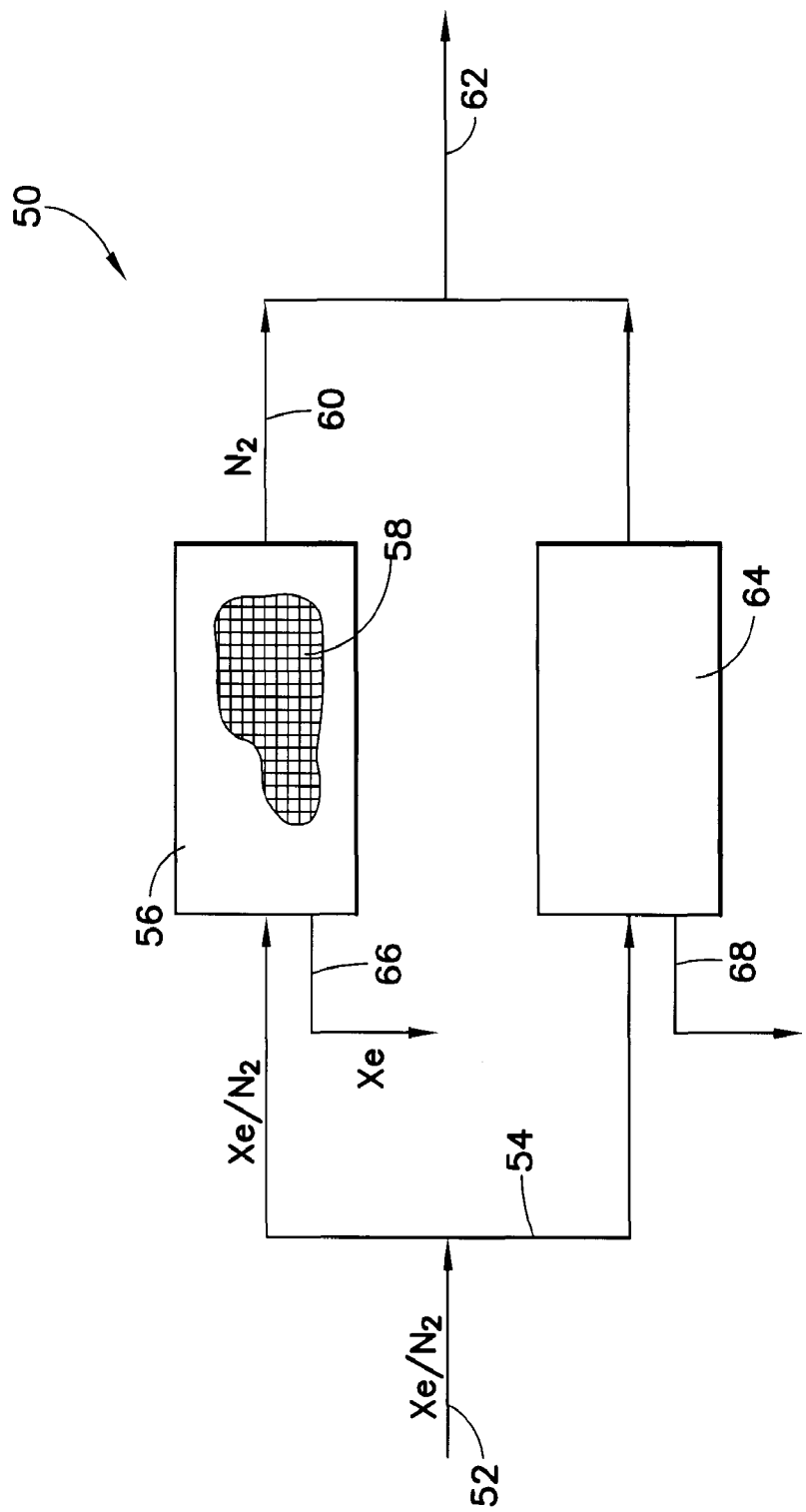
FIG. 2 is a schematic representation of a xenon/nitrogen separation system, in which a mixture of such gases is processed to recover the xenon component.

FIG. 2 is a schematic representation of a xenon/nitrogen separation system 50, in which a mixture of such gases is processed to recover the xenon component. The xenon/nitrogen gas mixture is introduced to the recovery system in line 52, and passed in manifold line 54 to an on-stream one of the two adsorbent vessels 56 and 64, each of which contains carbon adsorbent selective for xenon adsorption, adsorbent 58 being shown in the partially cutaway view of adsorbent vessel 56 in FIG. 2. During operation, one of the two adsorbent vessels 56 and 64 is on-stream, actively capturing xenon, while the other adsorbent vessel is off-stream, being regenerated or otherwise awaiting switching of the respective vessels, upon achievement of a requisite level of capture of xenon gas from the xenon/nitrogen gas stream being processed in the separation system 50.

Thus, the feed lines, discharge lines and manifold lines of the separation system 50 may be suitably valved to accommodate such alternating of the respective vessels between onstream and off stream conditions, and such valves may be operatively arranged for control by a cycle timer system or other control arrangement, to ensure continuity of operation.

In the system as depicted in FIG. 2, the vessel 56 may be the onstream vessel, with the xenon/nitrogen gas mixture entering such vessel from a manifold line 54, xenon being captured on the carbon adsorbent 58 therein, and nitrogen gas as the non-adsorbed species being discharged from the system in line 62. Concurrently, the vessel 64 is off-stream, and may be subjected to regeneration operation, e.g., by heating of the vessel and adsorbent contained therein, to effect desorption of previously adsorbed xenon gas, which is discharged from vessel 64 in discharge line 68, from which the xenon may be recycled, packaged, or subjected to other use or disposition.

Subsequently, when vessel 56 has completed its adsorption cycle, switchover takes place, and the xenon/nitrogen mixture then is flowed from manifold line 54 to vessel 64 for capture of xenon on the adsorbent in vessel 64 and discharge of nitrogen to the discharge manifold 60 and discharge line 62. Vessel 56 thereupon will be regenerated, to release the xenon previously adsorbed on the adsorbent 58, so that it is removed from vessel 56 in discharge line 66 and then recycled, package, or subjected to other use or disposition.

FIG. 3 is a schematic representation of a series-connected array of adsorbent vessels 80, 82 and 84, which may be utilized for recovery of high-value gas. The influent gas including one or more high-value gas species therein flows in inlet line 92 into adsorbent vessel 80 containing adsorbent 86 for capture on such adsorbent of the high-value gas of interest. The resulting contacted gas then flows in transfer line 94 to adsorbent vessel 82 containing adsorbent 88 therein, for contacting with such adsorbent, following which the resulting contacted gas flows in transfer line 96 to adsorbent vessel 84 containing adsorbent 90, from which finally contacted gas is discharged in effluent line 98. The respective vessels in the series arrangement shown can each be of different sizes and shapes, as shown.

FIG. 4 is a schematic representation of series-connected arrangement of adsorbent vessels 100 and 102, in which each adsorbent vessel contains multiple adsorbent beds of different adsorbent media. Influent gas in line 116 enters adsorbent vessel 100 containing a composite adsorbent including an adsorbent 104 and different adsorbent 106. The contacted gas resulting from such contacting with adsorbents 104 and 106 then flows in transfer line 118 to adsorbent vessel 102, containing adsorbents 108, 110 and 112. The gas resulting from such contacting with adsorbents 108, 110 and 112 then is discharged from adsorbent vessel 102 in discharge line 120. The gas in flowing through the respective adsorbent vessels 100 and 102 thereby is contacted with the five different adsorbents 104, 106, 108, 110 and 112.

Figure 5:
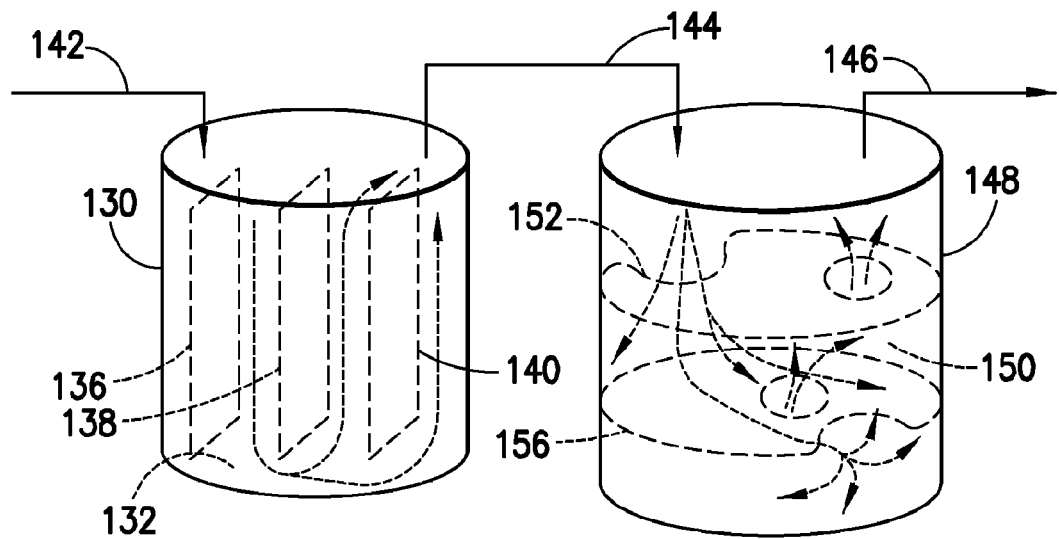
FIG. 5 is a schematic representation of a series-connected arrangement of adsorbent vessels, in which the vessels contain an array of flow-directing plate elements, for achievement of desired hydrodynamic processing of a gas stream to be contacted with adsorbent media in the respective vessels.

FIG. 5 is a schematic representation of a series-connected arrangement of adsorbent vessels 130 and 148, in which the vessels contain an array of flow-directing plate elements, for achievement of desired hydrodynamic processing of a gas stream to be contacted with adsorbent media in the respective vessels. Adsorbent vessel 130 receives influent gas from feed line 142, and contains flow-directing baffles 136, 138 and 140, in the interior volume 132 of the vessel. As a result, influent gas from feed line 142 is diverted along an extended length flow path for extensive contacting with adsorbent in the vessel (not shown for clarity). The respective baffles 136, 138 of 140 are as illustrated, vertically oriented in flow-directing positions. The gas flowing through the baffled path thereafter is discharged from vessel 130 and flows in transfer line 144 to adsorbent vessel 148. The interior volume 150 of adsorbent vessel 148 contains horizontally spaced-apart baffle plates 152 and 156, each of which has open areas therein defining an extended length flow path for the gas introduced into the interior volume 150 from transfer line 144 and thereafter discharged from vessel 148 in discharge line 146.

It will be appreciated from FIG. 5 that any suitable arrangements and orientation of baffle plates may be employed, to provide specific orientation of gas flow in the interior volume of the adsorbent-containing vessel, to ensure full and complete contacting of the gas with the adsorbent media in the respective vessels (not shown in either vessel 130 or 148).

Figure 6:
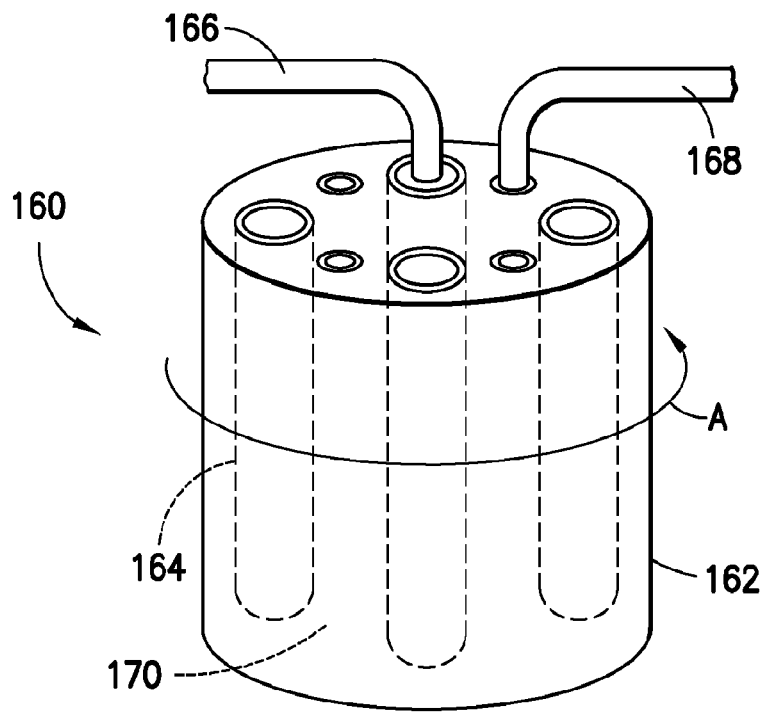
FIG. 6 is a schematic representation of a multiple adsorbent vessel arrangement, in which a housing contains the respective adsorbent vessels and is rotated in carousel fashion, to successively couple inlet and outlet conduits with a specific one of the multiple adsorbent vessels.

FIG. 6 is a schematic representation of a multiple adsorbent vessel arrangement, in which a housing 162 contains the respective adsorbent vessels 164 in the interior volume 170 of the housing. The housing is mounted on a suitable rotatable support, so that the housing is rotated in the direction indicated by arrow A in FIG. 6, in carousel fashion, to successively couple inlet and outlet conduits 166 and 168, respectively, with a specific one of the multiple adsorbent vessels. In this manner, influent gas is flowed into an adsorbent vessel and non-adsorbed gas is discharged therefrom, for a specific length of time, until the adsorbed gas loading on the adsorbent in the specific onstream vessel has reached a maximum or otherwise predetermined extent.

Following this, the carousel is rotated to uncouple the inlet and outlet conduits from the onstream vessel, and thereafter to engage same with the next succeeding adsorbent vessel in the circumferentially successive arrangement of vessels. For this purpose, the couplings between the inlet and outlet conduits and the inlet and outlet ports of the successive vessels may be of a quick-connect/quick-disconnect character, to accommodate the changeover in the sequence of vessels, as gas recovery operation proceeds.

FIG. 7 is a schematic representation of an adsorbent vessel 180, containing an adsorbent bed 188, and coupled with gas inlet line 182 and gas outlet line 190. From the inlet line 182, gas flows to the distributor member 200 having multiple gas flow orifices about the perimeter thereof, in the interior volume 186 of the vessel. Thus, gas is flowed into the inlet line 182 in the direction indicated by arrow A, distributed by the distributor member 200 over the full cross-section of the adsorbent bed 188, and discharged in gas outlet line 190 in the direction indicated by arrow B. The influent gas in this arrangement contains a sorbable gas that is captured by the adsorbent bed 188, so that sorbables-depleted effluent is discharged in outlet gas line 190.

FIG. 8 is a schematic vertical elevation view, in cross-section, of an adsorbent vessel to 10 containing a showerhead device 216 by which influent gas is introduced for contacting with the adsorbent bed 212 in the vessel. The showerhead device 216 is disposed in the interior volume 214 of the vessel, and arranged to receive influent gas from feed line 218 connected with the showerhead device 216. The showerhead device 216 includes discharge openings on the lower discharge face of such device, so that gas is distributed across the full cross-section section of the bed of adsorbent in the vessel.

FIG. 9 is a schematic vertical elevation view, in cross-section, of an adsorbent vessel 230 containing in the interior volume 240 thereof a manifold device 236 with nozzles 238 by which influent gas is introduced for contacting with the adsorbent bed 250 in the vessel. The manifold device 236 is joined in flow supplying relationship to gas feed line 234. The number and arrangement of nozzles 238 may be widely varied, to achieve the desired pressure drop and flow distribution characteristics desired for the contacting of gas with the adsorbent bed 250.

Figure 10:
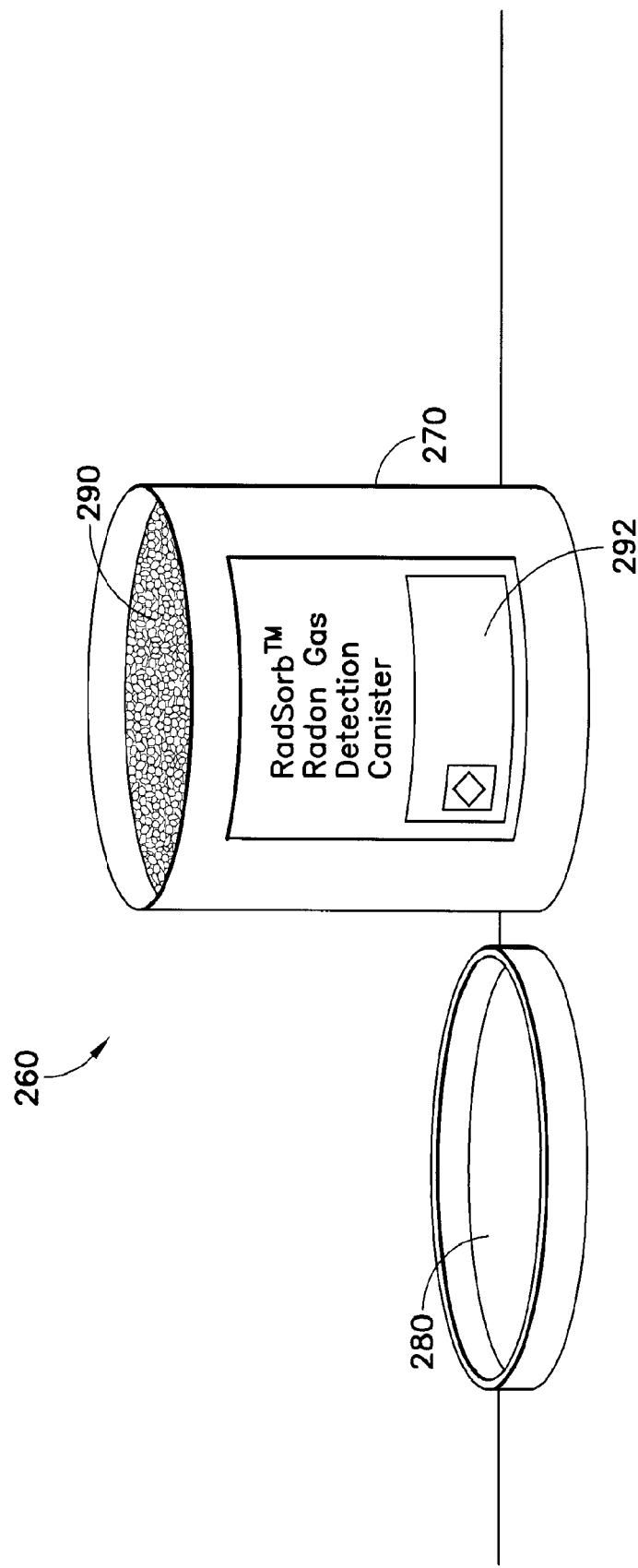
FIG. 10 is a perspective front elevation view of an adsorbent canister having utility for detection and monitoring of radon gas.

FIG. 10 is a perspective front elevation view of an adsorbent canister 260 having utility for detection and monitoring of radon gas. The canister 260 includes a can-type container 270 containing a quantity of carbon adsorbent 290 having suitable selectivity for radon gas. The container 270 has a cap 280 that is sized for engagement with the upper open end of the container 270, preferably to maintain a gas-tight seal of the canister, prior to removal of the cap 280 from the container 270, to expose the carbon adsorbent 294 for sorption of radon gas that is present in the environment of the canister.

The canister as shown may have a printed instructions label 292 on an exterior surface thereof, to facilitate use of the canister. The printed instructions on the label 292 may for example direct the user to uncap the canister and to leave the open canister in place in a specific environment, such as a closed room in a dwelling structure or office building, for a specified period of time, following which the container 270 is recapped with cap 280. The canister then can be sent to an analytical chemistry laboratory, for an assessment of the gas that has been adsorbed by the carbon adsorbent 290 during the period of exposure of such sorbent material to the environment being monitored. The carbon adsorbent 290 used in such canister 216 may be of any suitable type having affinity for radon gas, and may for example comprise a PVDC-based adsorbent material that has been processed, e.g. by water or steam treatment, and temperature and pressure conditions of specific character, to provide the carbon adsorbent with a predetermined pore size, pore size distribution, porosity density, radon loading characteristics, etc.

FIGS. 11-24 show various views of details of a fluid capture vessel that may be employed in the practice of the present disclosure, to recover sorbable gas in specific applications.

Figure 11:
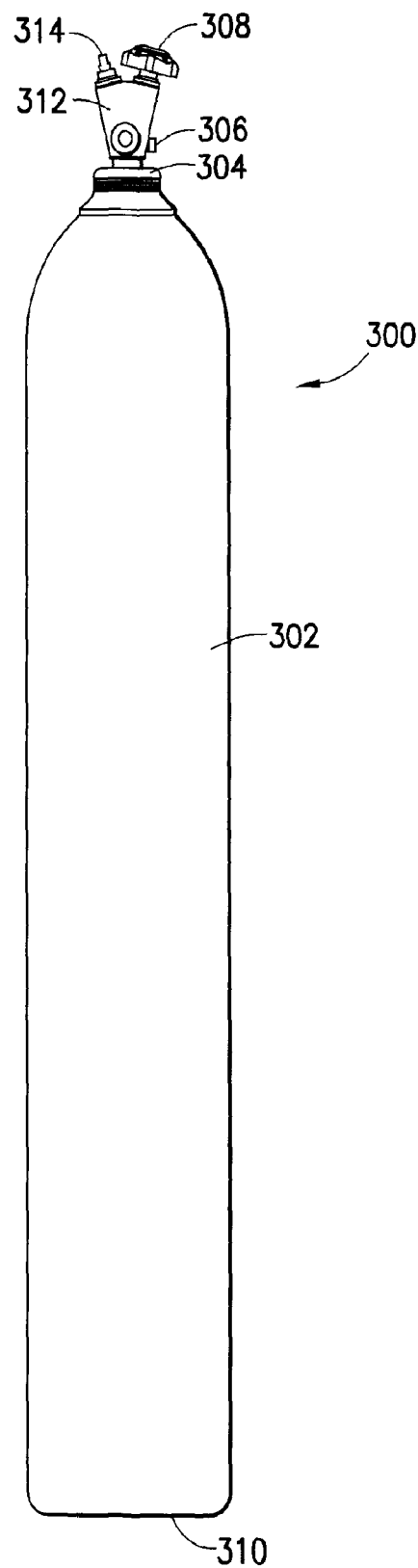
FIG. 11 is a vertical elevation view of a fluid capture vessel that may be employed to recover high value gas from a process or environment in which same is present.

FIG. 11 is a vertical elevation view of a fluid capture vessel 300 that may be employed to recover high value gas from a process or environment in which same is present. The fluid capture vessel 300 includes a main cylindrical body 302 having a generally flat lower peripheral surface, whereby the vessel may be maintained in an upstanding vertical position on a floor or other support surface. The vessel includes a neck portion 304 to which is secured, e.g., by threadable engagement, a valve head 312. The main cylindrical body 302 can be of any suitable size. In one preferred embodiment, such cylindrical body encloses a volume of 49 L.

The valve head 312 includes a manual hand wheel 308, which, as in other embodiments, may be replaced by a valve actuator of automatic character. The valve head is a two-port valve in the illustrated embodiment, with a fill port 306 equipped with a burst pressure device, e.g., for safety when the vessel is in a storage mode, and with a dispensing port 314.

Figure 12:
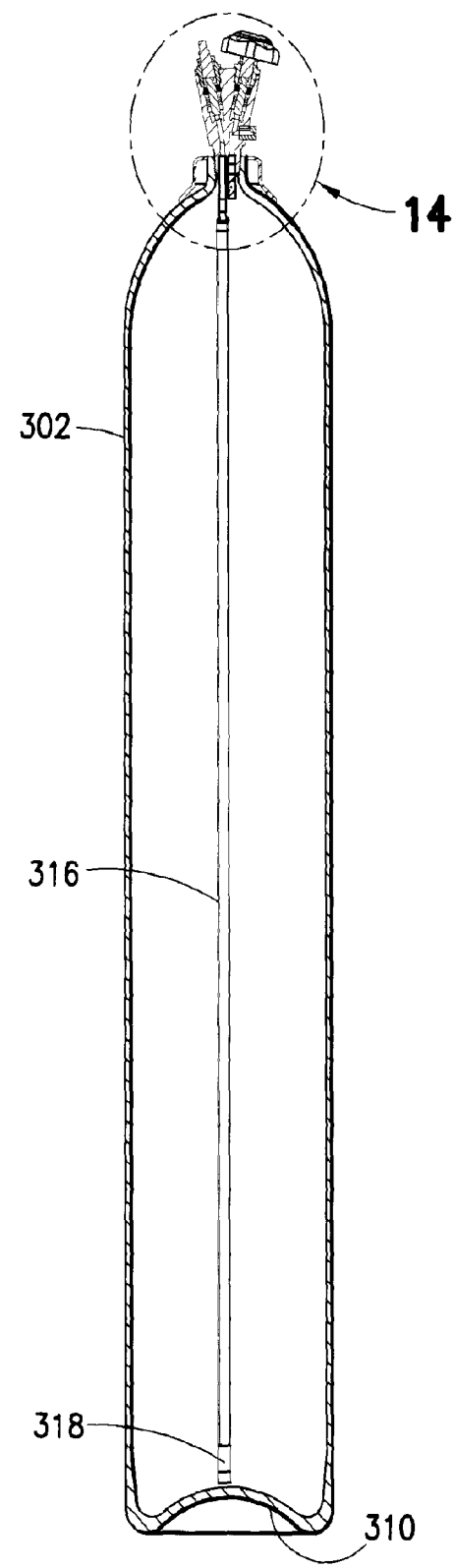
FIG. 12 is a vertical elevation view of the fluid capture vessel of FIG. 11, in cross-section section, showing the internal elements thereof.

FIG. 12 is a vertical elevation view of the fluid capture vessel of FIG. 11, in cross-section section, showing the internal elements thereof. As shown, the interior volume of the vessel contains a dip tube 316 for dispensing of gas from the vessel, with a lower dip tube portion 318.

Figure 13:
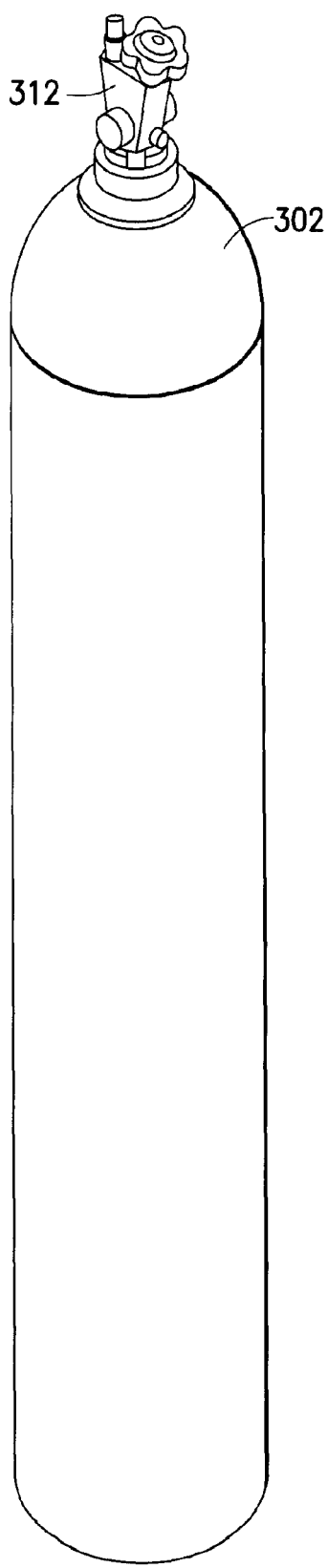
FIG. 13 is a perspective view of the fluid capture vessel of FIGS. 11 and 12.

FIG. 13 is a perspective view of the fluid capture vessel of FIGS. 11 and 12.

Figure 14:
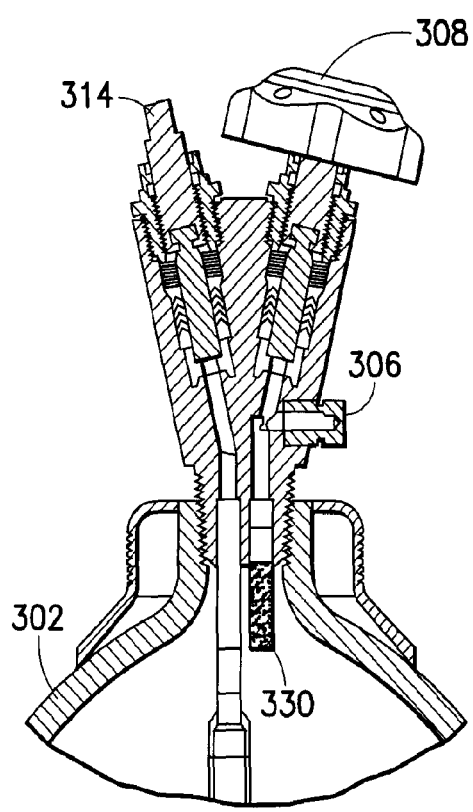
FIG. 14 is a cross-sectional elevation view of an upper portion of the fluid capture vessel of FIG. 11.

FIG. 14 is a cross-sectional elevation view of an upper portion of the fluid capture vessel of FIG. 11. As shown, the fill port 306 is arranged in flow communication with a filter 330, to ensure that gas is free of particulate matter and solid contaminants.

FIG. 15 is a perspective view of the valve head and dip tube assembly of the fluid capture vessel of FIGS. 11-14.

FIG. 16 is an exploded perspective view of the valve head and dip tube assembly of FIG. 15.

FIG. 17 is an exploded perspective view of an upper portion of the valve head and dip tube assembly of FIG. 15, showing details thereof. The parts and components of the dip tube assembly are numbered correspondingly with the corresponding parts and components shown in FIGS. 11-16. The dip tube assembly includes dip tube 316, connector adapter tube 332, and reducer 334.

FIG. 18 is an exploded perspective view of a lower portion of the dip tube assembly of FIG. 15, showing the dip tube 316, and a filter element 318 disposed at a lower end of the dip tube.

FIGS. 19-23 show various views of the valve head of the fluid capture vessel, in which components and parts are numbered correspondingly with respect to FIGS. 11-18.

Figure 19:
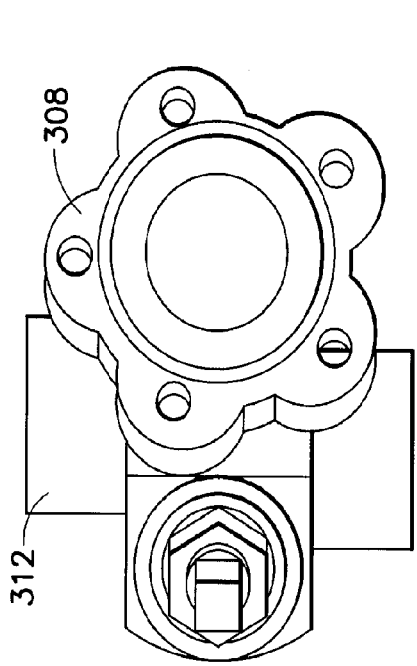
FIG. 19 is a top plan view of the valve head of the fluid capture vessel of FIGS. 11-14.

FIG. 19 is a top plan view of the valve head of the fluid capture vessel of FIGS. 11-14.

Figure 20:
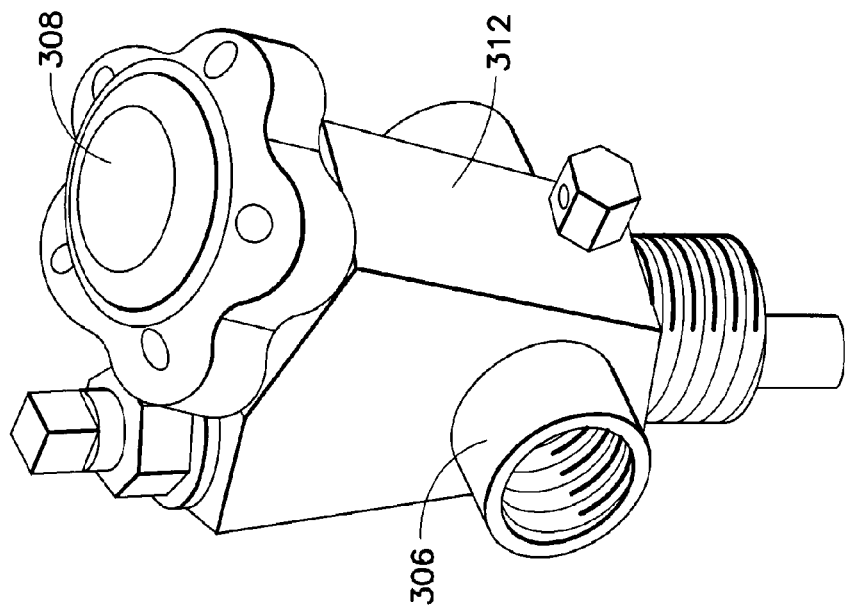
FIG. 20 is a perspective view of the valve head of the fluid capture vessel of FIGS. 11-14.

FIG. 20 is a perspective view of the valve head of the fluid capture vessel of FIGS. 11-14.

Figure 21:
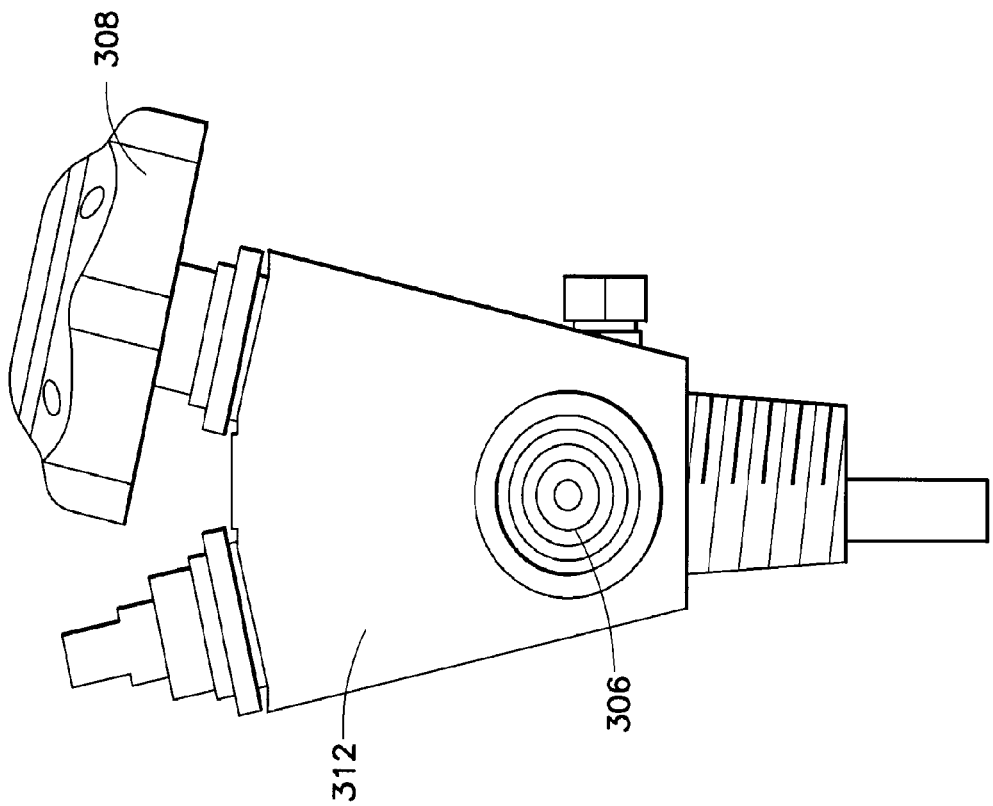
FIG. 21 is a front elevation view of the valve head of the fluid capture vessel of FIGS. 11-14.

FIG. 21 is a front elevation view of the valve head of the fluid capture vessel of FIGS. 11-14.

Figure 22:
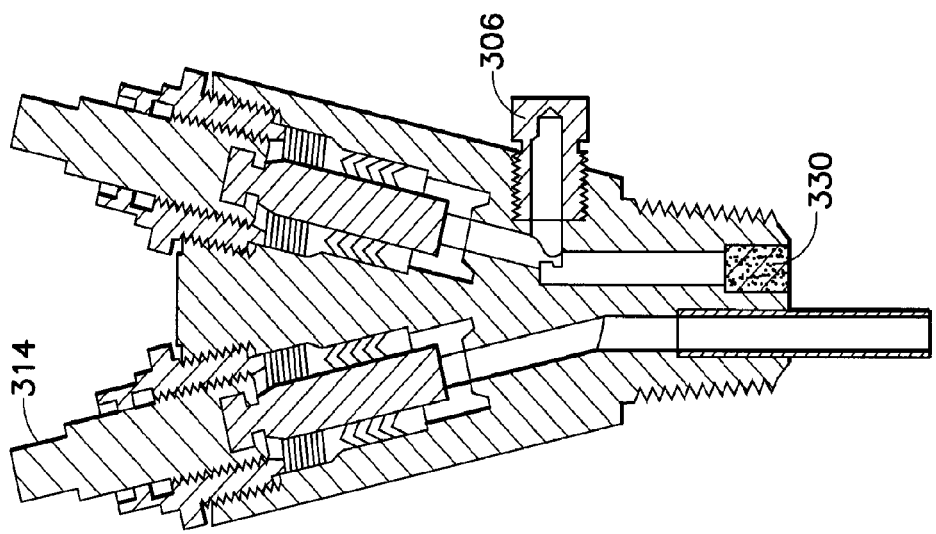
FIG. 22 is an elevation view, in cross-section, of the valve head of the fluid capture vessel of FIGS. 11-14.

FIG. 22 is an elevation view, in cross-section, of the valve head of the fluid capture vessel of FIGS. 11-14.

Figure 23:
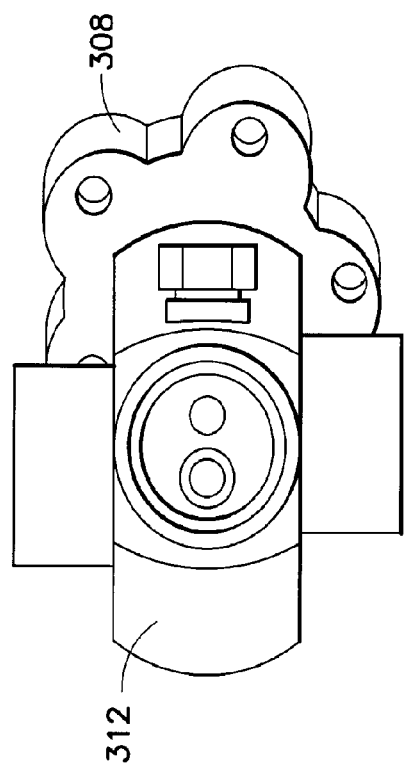
FIG. 23 is a bottom plan view of the valve head of the fluid capture vessel of FIGS. 11-14.

FIG. 23 is a bottom plan view of the valve head of the fluid capture vessel of FIGS. 11-14.

Figure 24:
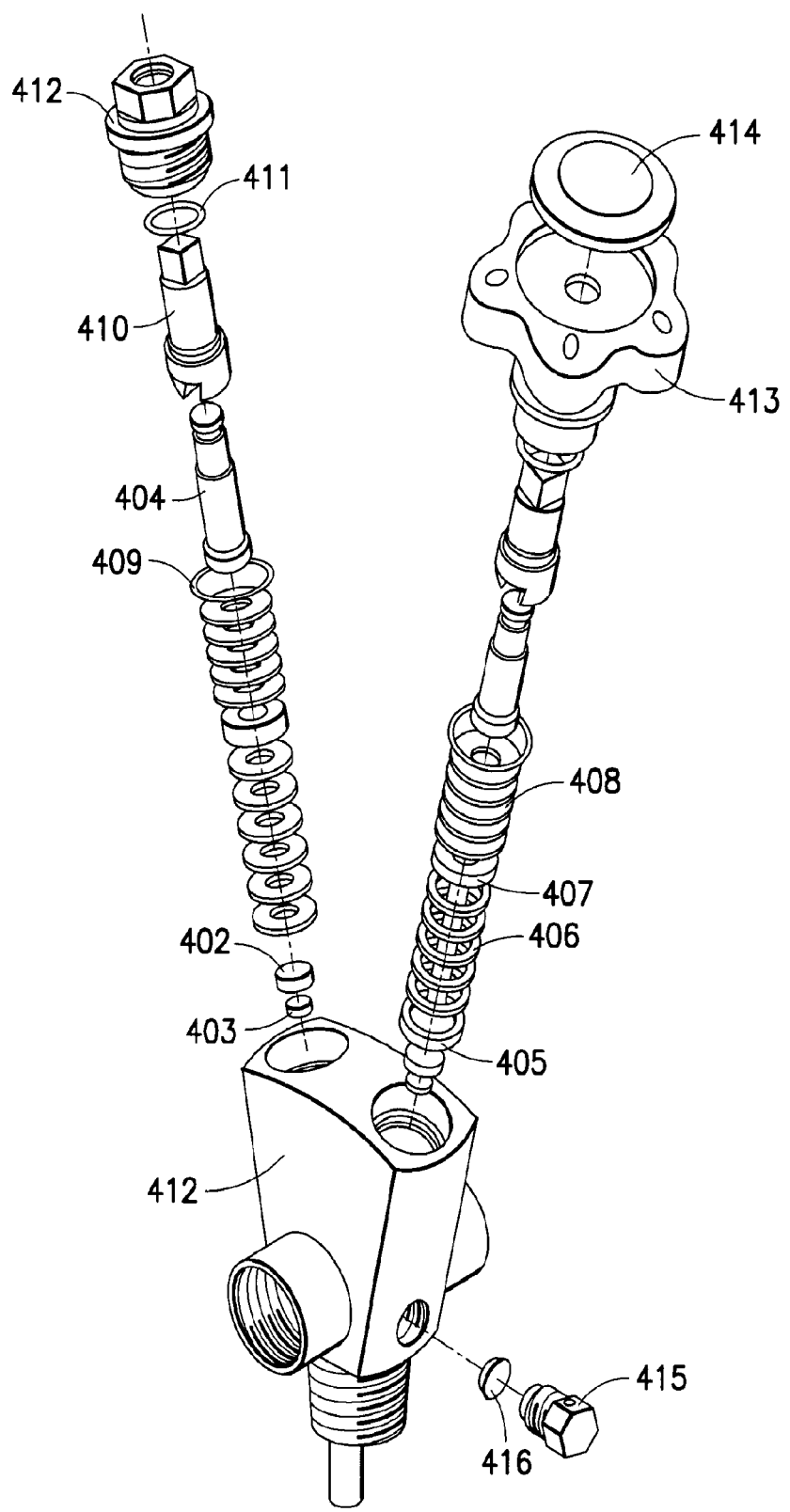
FIG. 24 is an exploded view of a valve head, of a type similar to that shown and described with reference to the fluid capture vessel of FIGS. 11-14.

FIG. 24 is an exploded view of a valve head, of a type similar to that shown and described with reference to the fluid capture vessel of FIGS. 11-14. The valve head 412 includes a valve body having an opening therein, in which is disposed a burst disc 416 and pressure relief device 415. Shown in exploded relationship to the valve body are a seat pin 403, a seat element 402, a gland nut gasket 409, a lower spindle 404, an upper spindle 410, an O-ring 411 and a gland nut 412. Also shown in exploded relationship to the valve body are a lower packing support 405, a chevron packing 406, an upper packing support 407, belleville washers 408, valve hand wheel 413 and hand wheel insert 414.

It will be recognized that the fluid capture vessel of the present disclosure may be configured in any of a variety of suitable forms, to receive recoverable gas for contacting with the adsorbent in the interior volume of the vessel, and with discharge of non-adsorbing gas for which the adsorbent has no sorptive affinity, during the contacting operation, if the recoverable gas is in mixture with such non-adsorbed gas.

Figure 25:
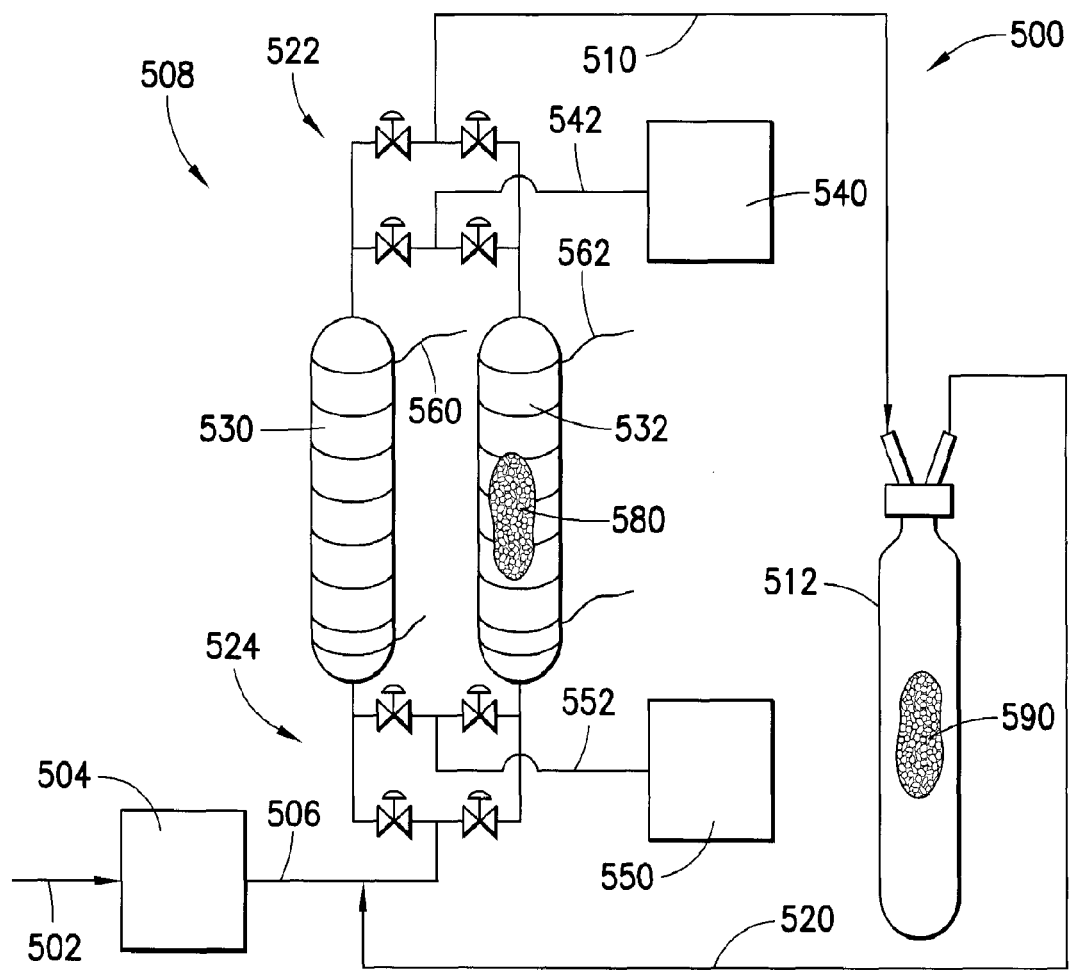
FIG. 25 is a schematic representation, in perspective, of a xenon recovery facility utilizing a fluid capture vessel of the type shown in FIGS. 11-24.

FIG. 25 is a schematic representation, in perspective, of a xenon recovery facility 500 utilizing a fluid capture vessel 512 of the type shown in FIGS. 11-24.

As shown in FIG. 25, xenon-containing gas mixture is flowed in feed line 502 to a vacuum pump 504 or other process interface. From the process interface, the xenon-containing gas mixture is flowed in line 506 to the xenon concentration unit 508. In the xenon concentration unit, the xenon gas may be concentrated to a higher than influent concentration. The enriched xenon gas then is flowed in flow line 510 to the xenon capture vessel 512.

The xenon-containing gas flows from line 510 into and through the carbon adsorbent 590 in such vessel, with xenon being sorptively taken up by the carbon adsorbent, and xenon-reduced gas being discharged from the vessel into recycle line 520, from which the xenon-reduced gas is recirculated to the feed gas line 506 to the xenon concentration unit.

The xenon recovery unit 508 as illustrated includes a pair of adsorbent vessels 530 and 532, each of which contains a bed 580 of carbon adsorbent. The beds are manifolded with an inlet manifold 524 and an outlet manifold 522, each of which is suitably valved for switching of operation of the respective vessels 530 and 532, so that one of the vessels is actively processing xenon-containing gas for adsorption thereof on the carbon adsorbent, while the other of the vessels is off-stream, and undergoing regeneration by purging during the off-stream period.

For this purpose, the outlet manifold 522 may be coupled with a source 540 of purge gas, so that purge gas can be flowed from such source in line 542 to the inlet manifold, for counter-current flow purging of the off-stream vessel. In this arrangement, the inlet manifold is coupled via purge gas exhaust lines 552 to a purge gas treatment unit 550, and purge gas discharged from the bed being regenerated in the off-stream vessel is treated in the purge gas treatment unit.

The on-stream vessel, subsequent to adsorption of xenon from the feed gas mixture containing same, to a predetermined extent or for a predetermined time, may thereupon be subjected to depressurization blowdown, to release previously adsorbed xenon to the outlet manifold 522, for flow in line 510 to the recovery vessel 512. Such vessel then is taken off line and subjected to regeneration, e.g., by purging, while the other previously off-stream vessel receives xenon-containing gas and carries out active adsorption processing to sorptively remove xenon from the influent gas mixture.

The vessels 530 and 532 in the xenon concentration unit 508 may also be arranged to effect desorption by heating, utilizing heating coils 560 and 562, respectively, as schematically illustrated in FIG. 25.

It will be recognized that the xenon concentration unit 508 is schematically shown and generally described, as regards the details of operation and construction thereof, inasmuch as such systems are of a well known and widely used character in the art.

A further variation of operation includes flow of the Xe-enriched gas mixture into the xenon capture vessel, with the xenon component of the gas being adsorbed on the carbon adsorbent, and with the non-adsorbed nitrogen gas being present in the interstices of the adsorbent bed and in the headspace above the adsorbent bed. Such arrangement permits the non-adsorbed nitrogen to be subsequently slowly bled from the vessel upon opening, prior to effecting desorption of the previously adsorbed xenon. For such purpose, the capture vessel containing adsorbed xenon, and non-adsorbed interstitial and headspace "free" nitrogen, may be chilled to temperature ensuring that the xenon is "tightly" sorptively held on the adsorbent, while the nitrogen is "blown off", i.e., released, from the vessel, prior to desorption of the xenon for reuse or further processing.

The use of a xenon capture vessel with a xenon concentration unit provides significant economic advantage. For example, in contrast to a circumstance in which nitrogen gas mixture enriched to a few percent of xenon is flowed into multiple empty (not containing adsorbent) vessels, for further separation processing and concentration of xenon, a single xenon capture vessel containing monolithic carbon adsorbent of the present disclosure can replace 29 empty vessels of comparable volumetric capacity. This in turn achieves a substantial savings in the number of vessels required, and in the associated storage, transport and processing costs.

The disclosure thus provides a method of recovering xenon gas from a process stream, material or environment containing same, by contacting xenon-containing gas from such process stream, material or environment with a carbon adsorbent of the character previously described, which is effective to sorptively capture the xenon.

In such method, the xenon-containing gas advantageously is treated prior to such contacting, to remove one or more components of the xenon-containing gas that are deleterious to said adsorbent. The one or more components can include at least one of xenon difluoride and nitrogen. For example, such components can include nitrogen, with the xenon-containing gas being treated to sorptively remove nitrogen therefrom, to yield a nitrogen-reduced gas for the further contacting. Such components can alternatively, or additionally, include xenon difluoride, e.g., with the xenon-containing gas can be treated to condense said xenon difluoride to a solid form, to yield a xenon difluoride-reduced gas for the further contacting.

Figure 26:
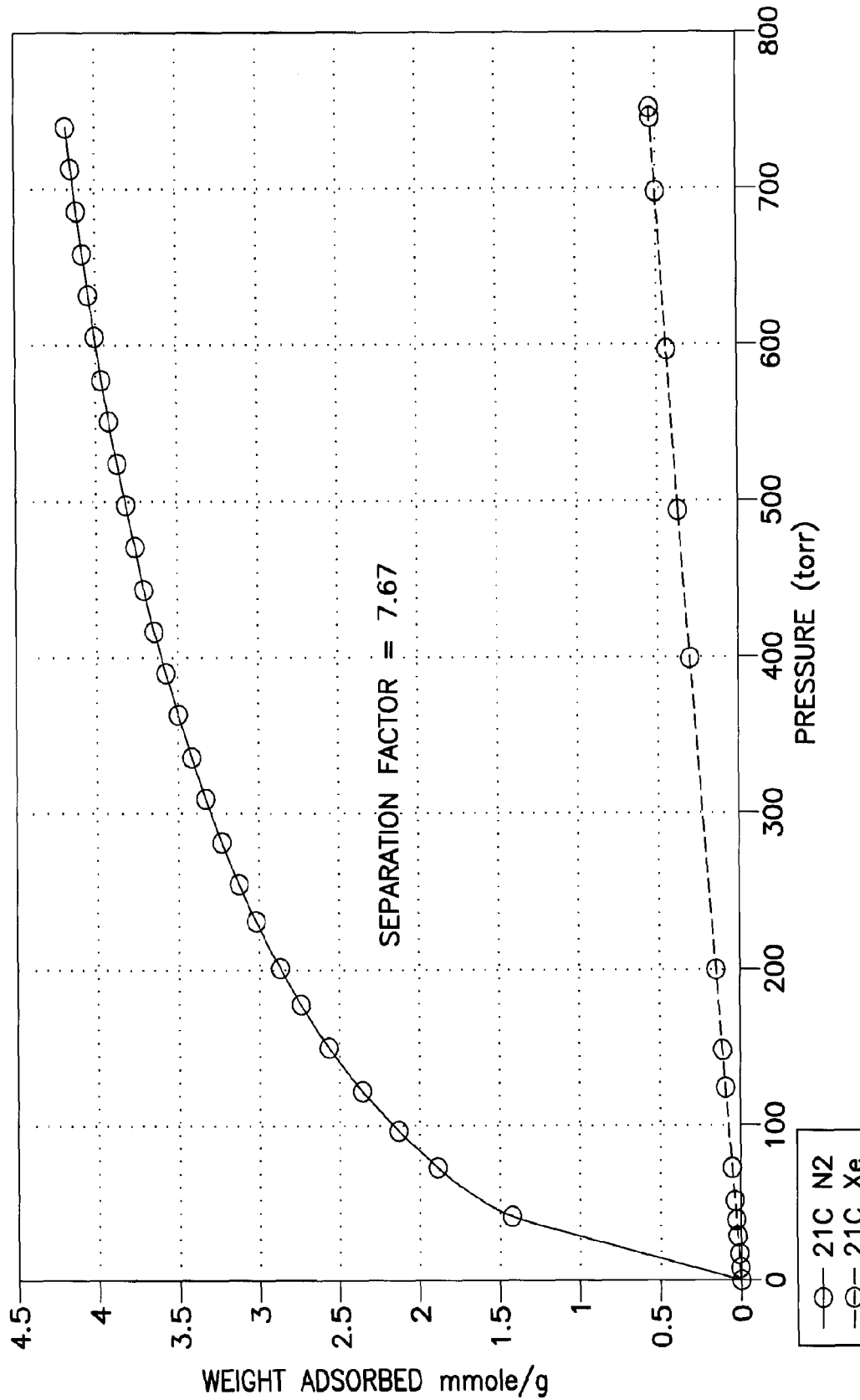
FIG. 26 is a graph of nitrogen and xenon adsorption isotherms on a carbon adsorbent adapted for xenon adsorption, as annotated with a calculated separation factor of 7.67 based on such isotherms.

FIG. 26 is a graph of nitrogen and xenon adsorption isotherms on a carbon adsorbent of the present disclosure that is particularly useful for xenon adsorption. The graph is annotated with a calculated separation factor of 7.67 based on such isotherms.

It will be appreciated that the present disclosure encompasses a wide variety of apparatus and methods utilizing carbon adsorbents.

In one such variant, the disclosure contemplates a xenon capture apparatus, comprising: a containment vessel; a carbon adsorbent of the present disclosure in the containment vessel, in which the carbon adsorbent is selective for xenon gas.

The xenon capture apparatus may include a containment vessel that is adapted for flow therethrough of xenon-containing gas, so that the carbon adsorbent selectively adsorbs same, and the vessel allows discharge therefrom of non-xenon gas component(s) of the xenon-containing gas. The xenon capture apparatus alternatively may include a containment vessel that is adapted for flow thereinto of the xenon-containing gas, without concurrent discharge of gas from the containment vessel.

The xenon capture apparatus may be arranged with the containment vessel in flow-receiving relationship to a source of xenon-containing gas. The xenon capture apparatus may be arranged with the source of xenon-containing gas comprising a xenon concentration unit that operates to increase xenon concentration of the xenon-containing gas from part-per-million to percentage levels. As another variant, the source of xenon-containing gas can include an ion implanter apparatus arranged to receive xenon difluoride cleaning gas from a xenon difluoride source. The xenon difluoride source may for example comprise a source vessel containing xenon difluoride on a support matrix.

In a further aspect, the disclosure contemplates a radon monitoring assembly, comprising:

a container:

a cap engageable with said container to enclose an interior volume of the container;

a carbon adsorbent in said container, such carbon adsorbent being selective for radon in relation to atmospheric gases; and written indicia constituting instructions for use of the radon monitoring assembly.

The written indicia may specify temporal exposure for such monitoring.

Another aspect of the disclosure relates to a method of detecting radon contamination in a locus susceptible to presence or incursion of radon, involving placement of a radon monitoring assembly as described above, in an uncapped state, in the target locus, to enable contact of the carbon adsorbent with ambient gas, and recapping the container after a predetermined period of time to provide a contained sample for analytical testing for radon contamination.

Another aspect of the disclosure relates to a method of recovering high-value gas from a process stream, material or environment containing same, by contacting the process stream, material or sample from such environment with a carbon adsorbent of the present disclosure, which is selective for such high-value gas.

The carbon adsorbent as mentioned earlier herein can be in a particulate or monolithic form. The carbon adsorbent can be a pyrolysis product of a polyvinylidene chloride resin, e.g., wherein the pyrolysis product has been processed following pyrolysis to modify porosity thereof for uptake of the high-value gas, e.g., by treatment including at least one of water, steam, penetration gas, elevated temperature and elevated pressure. Such adsorbent can be in a monolithic form.

The adsorbent can also be deployed in multiple adsorbent vessels through which the process stream, material or sample from the target environment is flowed for contacting. In various embodiments, at least some of the multiple adsorbent vessels can be of differing sizes, and/or the multiple adsorbent vessels can contain different adsorbents. The arrangements can include arrangements in which at least one of the multiple adsorbent vessels contains multiple adsorbents therein. The vessels can contain baffles, plates or other flow-directing elements. The vessels can be arranged in a unitary array for rotation, for feeding of gas through a selected one of the multiple vessels at a time.

In various of the foregoing arrangements, the process stream, material or sample from the target environment can be flowed through a showerhead device or a nozzle-equipped manifold to the adsorbent for contacting.

In another aspect, the disclosure relates to a system for recovering high-value gas from a process stream, material or environment containing same, in which the system includes a carbon adsorbent of the present disclosure, arranged for contacting the process stream, material or sample from the target environment to sorptively capture the high-value gas. The carbon adsorbent can be a pyrolysis product of a polyvinylidene chloride resin, e.g., a pyrolysis product that has been processed following pyrolysis to modify its porosity for uptake of the high-value gas, such as by treatment including at least one of water, steam, penetration gas, elevated temperature and elevated pressure. The carbon adsorbent can be in a monolithic or particulate form for such purpose.

In this system, the adsorbent can be deployed in multiple adsorbent vessels through which the process stream, material or sample from the environment is flowed for contacting with the adsorbent. Various embodiments include arrangements in which: at least some of the multiple adsorbent vessels are of differing sizes; the multiple adsorbent vessels contain different adsorbents; at least one of the multiple adsorbent vessels contains multiple adsorbents therein; the vessels contain baffles, plates or other flow-directing elements; the vessels are arranged in a unitary array for rotation, for feeding of gas through a selected one of the multiple vessels at a time; and arrangements in which the process stream, material or sample from the target environment is flowed through a showerhead device or a nozzle-equipped manifold to the adsorbent for contacting.

The disclosure accordingly contemplates a wide variety of applications in use of a carbon adsorbent having a bulk density in a range of from 750 to 1300 kg per cubic meter ($kg/m^3$), and a porosity in which the majority of pores are in a range of from 5 to 8 Angstroms. Such carbon adsorbent has particular utility for recovery of xenon, as well as utility for sorptive capture of other small molecular species, and for storage and subsequent dispensing of such species.

While the invention has been has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A method of recovering xenon gas from a process stream, material or environment containing same, comprising contacting xenon-containing gas from said process stream, material or environment with a carbon adsorbent effective to sorptively capture same, free of or with reduced concentration of fluid species initially present with said xenon in said xenon-containing gas in said process stream, material or environment, wherein the carbon adsorbent has a bulk density in a range of from 750 to 1300 kg per cubic meter ($kg/m^3$), and a porosity in which the majority of pores are in a range of from 5 to 8 Angstroms.

2. The method of claim 1, wherein the xenon-containing gas is treated prior to said contacting, to remove one or more components of said xenon-containing gas that are deleterious to said adsorbent.

3. The method of claim 2, wherein said one or more components include xenon difluoride.

4. The method of claim 2, wherein said one or more components include nitrogen.

5. The method of claim 1, wherein said xenon-containing gas is supplied by a xenon recovery process concentrating xenon in a source gas mixture, from part per million levels to percentage levels.

6. The method of claim 1, wherein said xenon-containing gas is supplied by a semiconductor manufacturing apparatus cleaning process utilizing xenon difluoride.

7. The method of claim 6, wherein the semiconductor manufacturing apparatus comprises an ion implanter apparatus.

8. The method of claim 6, wherein the cleaning process comprises a plasma cleaning process.

9. The method of claim 6, wherein the cleaning process does not employ plasma.

10. The method of claim 1, wherein said carbon adsorbent is characterized by a volumetric sorptive capacity for xenon, measured at temperature of 273° Kelvin and 1 bar pressure, of from 125 to 150 volumes xenon/volume carbon adsorbent, and a separation factor $\alpha_{Xe,N}$, in relation to xenon and nitrogen, which is in a range of from 2 to 12.

11. A xenon capture apparatus, comprising:
a containment vessel adapted for arrangement in flow-receiving relationship to a source of xenon-containing gas; and
a carbon adsorbent in the containment vessel, wherein the carbon adsorbent is selective for xenon gas, and wherein the carbon adsorbent has a bulk density in a range of from 750 to 1300 kg per cubic meter (kg/m³), and a porosity in which the majority of pores are in a range of from 5 to 8 Angstroms, wherein the apparatus comprises one or more of the arrangements (A)-(D):
(A) the containment vessel is arranged in flow-receiving relationship to a source of xenon-containing gas, and the carbon adsorbent (i) has a volumetric sorptive capacity for xenon, measured at temperature of 273° Kelvin and one bar pressure, of from 125 to 150 volumes xenon/volume carbon adsorbent, and (ii) is characterized by a separation factor $\alpha_{Xe,N}$, in relation to xenon and nitrogen, which is in a range of from 2 to 12;
(B) the containment vessel is arranged in flow-receiving relationship to a source of xenon-containing gas, and said source of xenon-containing gas comprises a xenon concentration unit increasing xenon concentration of said xenon-containing gas from part per million to percentage levels;
(C) the containment vessel is arranged in flow-receiving relationship to a source of xenon-containing gas, and said source of xenon-containing gas comprises an ion implanter apparatus arranged to receive xenon difluoride cleaning gas from a xenon difluoride source; and
(D) the containment vessel is arranged in flow-receiving relationship to a source of xenon-containing gas, and said source of xenon-containing gas comprises a source vessel containing xenon difluoride on a support matrix.

12. The xenon capture apparatus of claim 11, wherein the containment vessel is arranged in flow-receiving relationship to a source of xenon-containing gas, and the carbon adsorbent (i) has a volumetric sorptive capacity for xenon, measured at temperature of 273° Kelvin and one bar pressure, of from 125 to 150 volumes xenon/volume carbon adsorbent, and (ii) is characterized by a separation factor $\alpha_{Xe,N}$, in relation to xenon and nitrogen, which is in a range of from 2 to 12.

13. The xenon capture apparatus of claim 11, wherein the containment vessel is arranged in flow-receiving relationship to a source of xenon-containing gas, and wherein said source of xenon-containing gas comprises a xenon concentration unit increasing xenon concentration of said xenon-containing gas from part per million to percentage levels.

14. The xenon capture apparatus of claim 11, wherein the containment vessel is arranged in flow-receiving relationship to a source of xenon-containing gas, and wherein said source of xenon-containing gas comprises an ion implanter apparatus arranged to receive xenon difluoride cleaning gas from a xenon difluoride source.

15. The xenon capture apparatus of claim 11, wherein the containment vessel is arranged in flow-receiving relationship to a source of xenon-containing gas, and wherein said source of xenon-containing gas comprises a source vessel containing xenon difluoride on a support matrix.

16. A carbon adsorbent, characterized by a bulk density in a range of from 750 to 1300 kg per cubic meter (kg/m³), a porosity in which the majority of pores are in a range of from 5 to 8 Angstroms, a separation factor $\alpha_{Xe,N}$, in relation to xenon and nitrogen, which is in a range of from 2 to 12, a volumetric sorptive capacity for xenon at 273° K and one bar pressure, of 125 to 150 volumes xenon/volume carbon adsorbent, and a thermal conductivity of 0.44-1.20 $Wm^{-1}K^{-1}$.

17. The carbon adsorbent of claim 16, in the form of a pyrolyzed monolith characterized by a bulk density in a range of from 800 to 1200 kg/m³.

18. The carbon adsorbent of claim 16, characterized by a volumetric sorptive capacity for xenon, measured at temperature of 273° Kelvin and one bar pressure, of from 125 to 145 440 volumes xenon/volume carbon adsorbent.

19. The carbon adsorbent of claim 16, characterized by a separation factor $\alpha_{Xe,N}$, in relation to xenon and nitrogen, which in a range of from 3 to 10.

20. The carbon adsorbent of claim 16, in the form of a pyrolyzed monolith formed as a pyrolysis product of a polyvinylidene chloride resin, characterized by a separation factor $\alpha_{Xe,N}$, in relation to xenon and nitrogen, which in a range of from 4 to 8.

* * * * *